(12) United States Patent
Cook et al.

(10) Patent No.: US 10,337,951 B2
(45) Date of Patent: Jul. 2, 2019

(54) APPARATUS AND METHOD FOR ASSESSING PLANT STEM STRENGTH

(71) Applicant: NEW YORK UNIVERSITY, New York, NY (US)

(72) Inventors: Douglas Cook, New York, NY (US); Daniel Robertson, Kennewick, WA (US); Margaret Julias, Abu Dhabi (AE); Shien Yang Lee, Abu Dhabi (AE)

(*) Notice: Subject to any disclaimer, the term of this patent is extended or adjusted under 35 U.S.C. 154(b) by 0 days.

(21) Appl. No.: 15/736,274

(22) PCT Filed: Jun. 14, 2016

(86) PCT No.: PCT/US2016/037434
§ 371 (c)(1),
(2) Date: Dec. 13, 2017

(87) PCT Pub. No.: WO2016/205244
PCT Pub. Date: Dec. 22, 2016

(65) Prior Publication Data
US 2018/0195929 A1 Jul. 12, 2018

Related U.S. Application Data

(60) Provisional application No. 62/175,885, filed on Jun. 15, 2015.

(51) Int. Cl.
*G01M 5/00* (2006.01)
*G01N 3/20* (2006.01)
*G01N 33/00* (2006.01)

(52) U.S. Cl.
CPC ........ *G01M 5/0025* (2013.01); *G01M 5/0075* (2013.01); *G01N 3/20* (2013.01); *G01N 33/0098* (2013.01); *G01N 2203/0266* (2013.01)

(58) Field of Classification Search
CPC .... G01M 5/0025; G01M 5/0075; G01N 3/20; G01N 33/0098; G01N 2203/0266
USPC .......................................................... 73/788
See application file for complete search history.

(56) References Cited

U.S. PATENT DOCUMENTS

| | | | | |
|---|---|---|---|---|
| 4,342,270 A * | 8/1982 | Lofgren | .................. | A01C 5/04 111/117 |
| 4,549,355 A * | 10/1985 | Sauer | ...................... | A01G 7/00 33/783 |
| 4,583,554 A * | 4/1986 | Mittelman | ........... | A61B 5/4533 600/587 |
| 4,726,175 A * | 2/1988 | Day, V | .................. | A01B 69/00 172/5 |
| 5,044,210 A | 9/1991 | Kuhn et al. | | |
| 5,228,454 A | 7/1993 | Siegler | | |
| 6,983,582 B1 | 1/2006 | Muckler | | |
| 7,401,528 B2 | 7/2008 | Deppermann et al. | | |

(Continued)

OTHER PUBLICATIONS

International Search Report and Written Opinion in PCT/US2016/037434, dated Sep. 1, 2016, 10 pages.

*Primary Examiner* — Max H Noori
(74) *Attorney, Agent, or Firm* — Foley & Lardner LLP

(57) ABSTRACT

Apparatus and methods for determining flexural rigidity of a plant. The apparatus includes a base and support hingedly coupled thereto. A contact element on the support engages the stem of plant. Force and angular displacement data are collected. Flexural rigidity of the plant stem is determined.

18 Claims, 18 Drawing Sheets

(56) References Cited

U.S. PATENT DOCUMENTS 7,987,735 B2    8/2011  Mann, III et al.
2007/0294994 A1*  12/2007  Deppermann ........... A01G 7/00
                                                      56/27.5

* cited by examiner

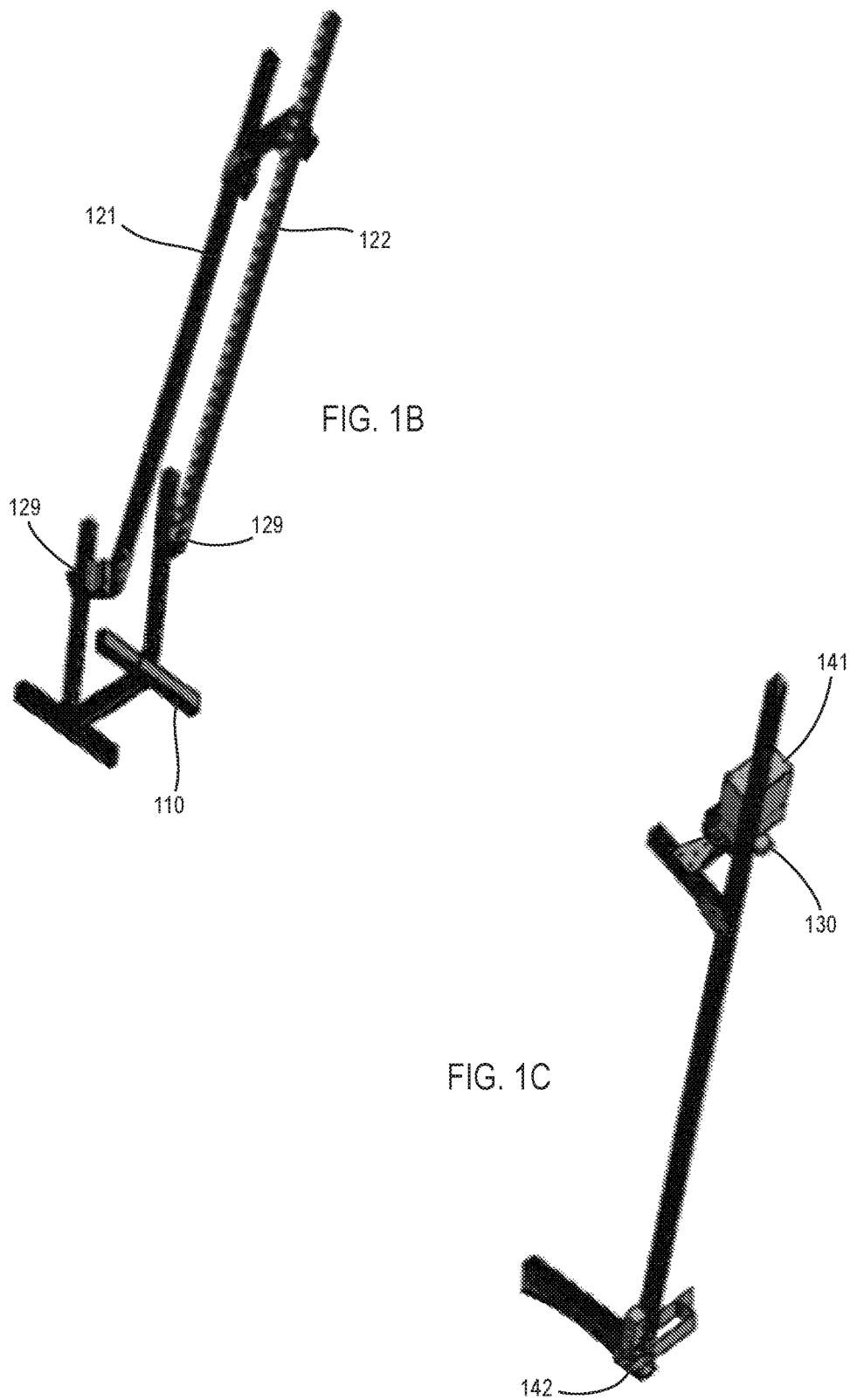

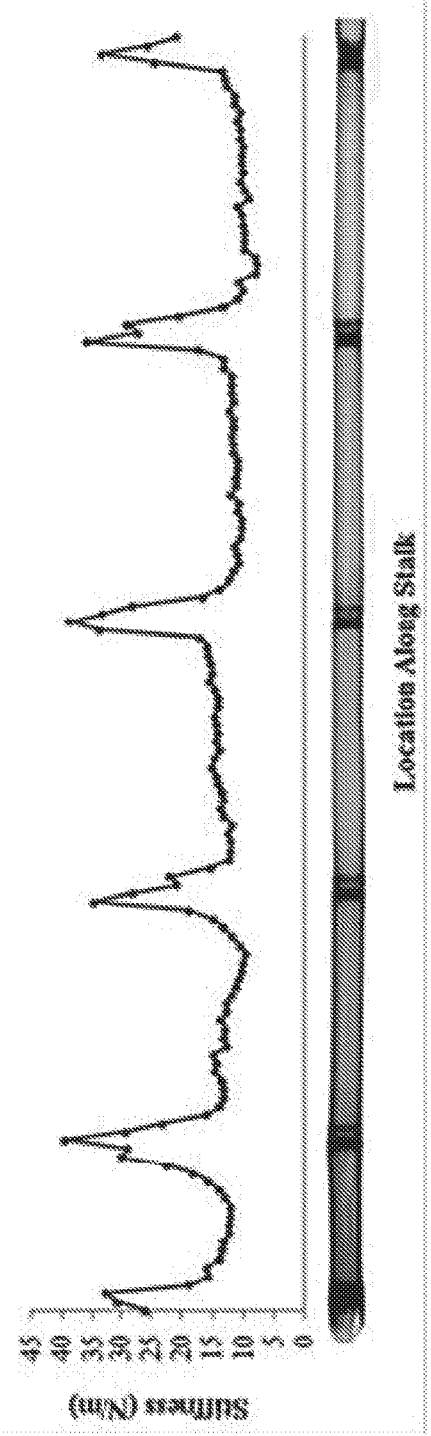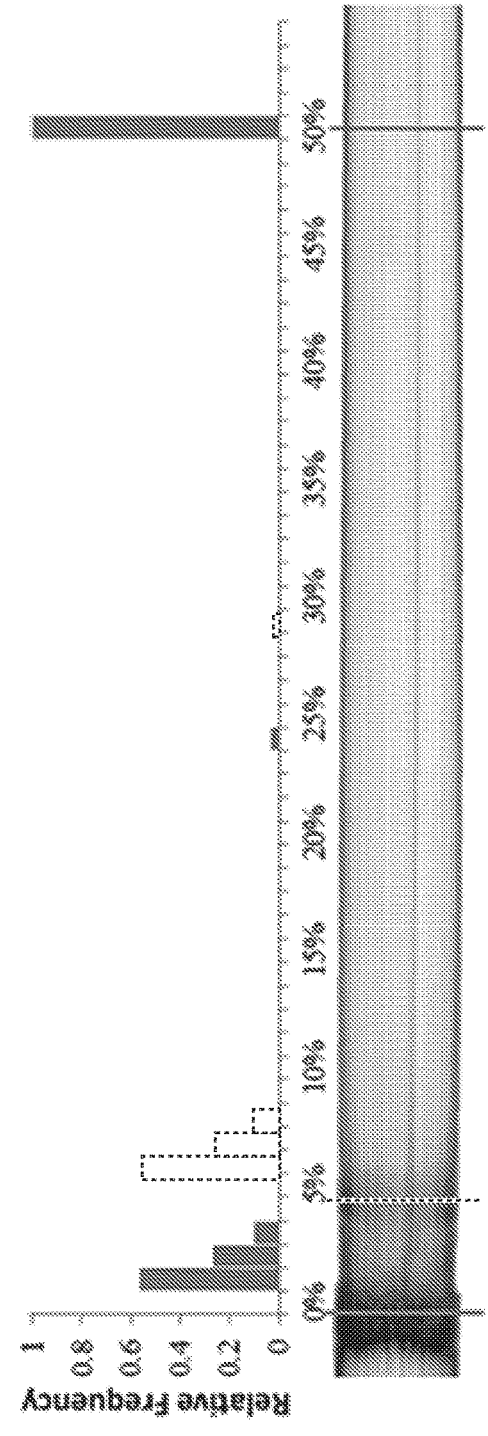

Corn

Giant reed

Bamboo

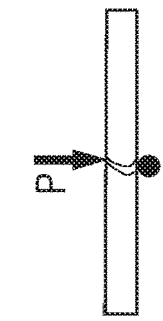
Three-point bending
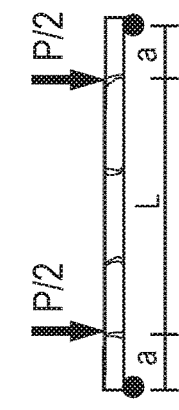
Four-point bending
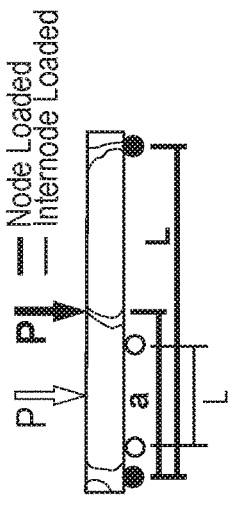
FIG. 12A
FIG. 12B
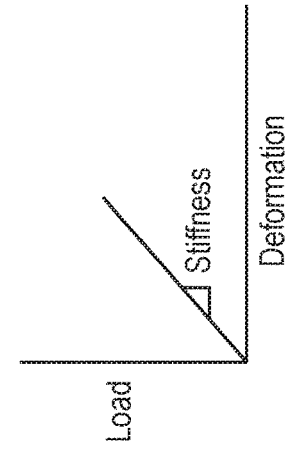
Transverse compression
FIG. 12C
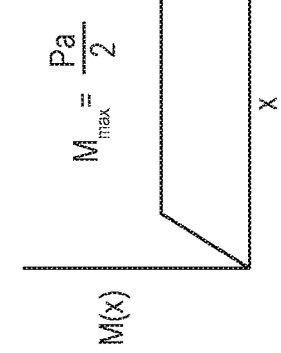
FIG. 12D
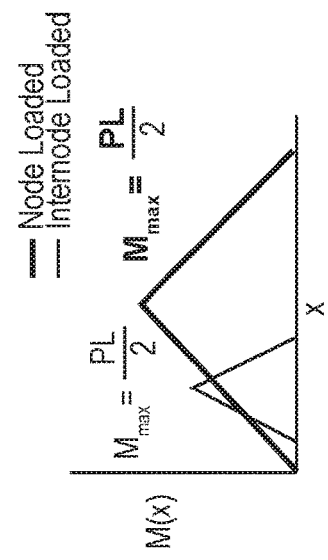
FIG. 12E
FIG. 12F

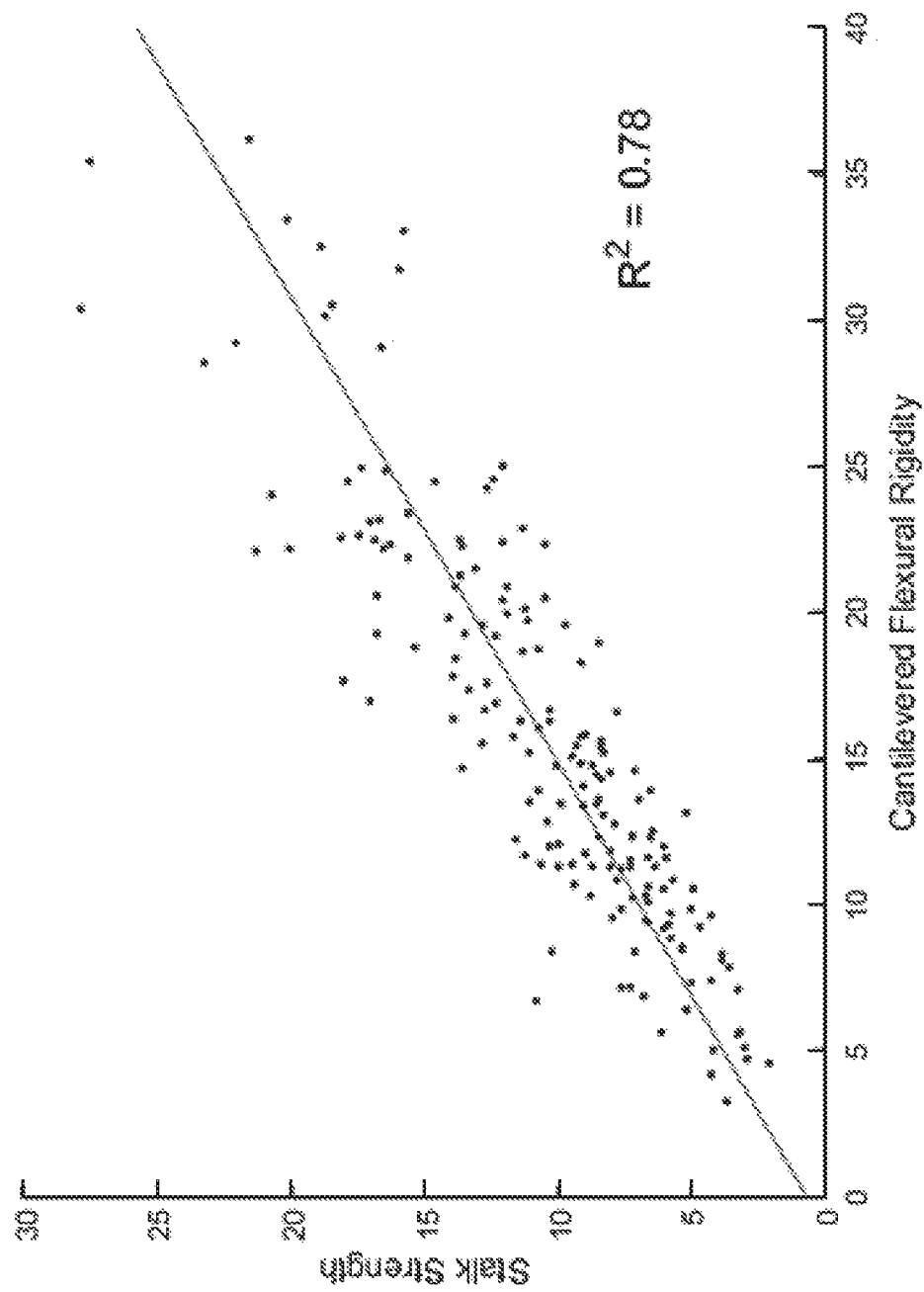

APPARATUS AND METHOD FOR ASSESSING PLANT STEM STRENGTH

CROSS-REFERENCE TO RELATED PATENT APPLICATIONS

This application is the U.S. national phase application under 35 U.S.C. § 371 of International Application No. PCT/US2016/037434, filed Jun. 14, 2016, which claims priority from U.S. Provisional Application No. 62/175,885, filed Jun. 15 2015, both incorporated herein by reference in their entirety.

FIELD OF THE INVENTION

The present invention generally relates to strength testing of plants.

BACKGROUND OF THE INVENTION

Breakage of plant stems, trunks (e.g., saplings), and/or stalks (collectively referred to as "stems") due to bending can drastically reduce crop yields. For example, maize stalk lodging (breakage of the plant stalk during wind and rain storms) reduces yields of by about 5% annually (Duvick, 2005). Such failures also prevent the development of higher yielding plant varieties because large and heavy grains and kernels cause premature stalk breakage. Increasing the bending strength of plant stems is therefore important to both current production and future development.

In plants, bending strength is affected by both genetic and environmental factors. Environmental pressures such as water availability, temperature, and soil composition can have strong effects on plants' strength. Structural failure is often caused by severe weather events. All of these factors make it difficult to distinguish between genetic and environmental effects on strength, even when collecting data across multiple years and across varied environments. An accurate method to quantify the bending strength of plants would enable improvements through selective breeding and genetic modification.

Various mechanical tests have been developed to measure stalk strength. Crush tests were developed and applied to excised maize stalk segments (Thompson, 1964; Zuber and Grogan, 1961) to select stronger stalks. Rind penetrometers have been used for recurrent selection and quantitative trait locus (QTL) mapping (Peiffer et al., 2013) of maize, and three-point bending has been used for QTL mapping and corn stalk characterization (Hu et al., 2013). Recent studies in other grass species have used similar approaches (Jin et al., 2009; Kokubo et al., 1991; Li et al., 2003; O'Dogherty et al., 1995).

Current methods of measuring stalk strength are labor-intensive and time consuming, making them unattractive to plant breeders. In general, prior art methods use indirect alternatives to predict or estimate strength. For example, geometric measurements such as diameter, chemical measurements such as lignin content or mechanical measurements such as force to pierce the stalk with a needle. Recent research has revealed that the predominant failure pattern (or failure modes) of maize stalks is a distinctive crease near the node (Robertson et al., 2015). Previous studies of stalk strength induce failure patterns that are substantially different, thus explaining their limited utility in addressing the problem of stalk lodging.

A tool which provides a, reliable, and quantitative measurement of stem strength, ideally replicating the type of breakage experienced in nature, would be very valuable to plant breeders as it would enable selective breeding for increased strength and reduced lodging propensity.

SUMMARY OF THE INVENTION

One embodiment of the invention relates to a testing apparatus for tipping or displacing a plant stalk/stem. This embodiment may utilize a hinged arm coupled to a base support by a hinge; an adjustable contact element to engage with the plant stalk stem; a force gauge associated with the contact element; a rotary encoder associated with the hinge and configured to detect angular displacement of the support.

Another embodiments of the invention relates to a method of determining the flexural rigidity of a plant comprising: setting a base adjacent to the plant, with the plant positioned within a groove in the base; adjusting a contact element along a support and aligning the contact element with a stem of the plant; angularly displacing the support and engaging the stem with the contact element to apply force to the stem; measuring force data concerning the force applied to the stem; measuring angular displacement of the support; calculating the flexural rigidity of the plant based on force and displacement data.

Another embodiments of the invention relates to a method of determining plant stem strength comprising: determining a height of a testing apparatus from ground; engaging the plant stem with the testing apparatus; detecting the force applied to the stem; displacing the plant stem; measuring the amount of displacement; and determining the flexural rigidity of the plant stem.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 1B illustrates a two-arm stem testing apparatus, FIG. 1C illustrates a single-arm stem testing apparatus.

FIG. 3(A) shows the bending moment at failure is shown for each test configuration. FIG. 3(B) shows the maximum bending moment applied at the internode region during each test. It should be noted that a significantly higher bending moment was experienced at the internode during the node-loaded tests than was required to fail to same section during the internode-loaded tests. This suggests that loading at the internode during three-point bending experiments induces premature failure.

FIG. 4A shows transverse compressive stiffness measured at 0.5-mm intervals along maize stalk. FIG. 4B shows an X-ray image of the same maize stalk is shown for physiological reference. Distinct peaks in the stiffness are seen to coincide with the nodal regions (dark bands in X-ray image).

FIG. 5A shows the distribution of normalized failure locations for node (shown at left) and internode loaded (shown at right) three-point bending tests of corn stalk. FIG. 5B shows the X-ray image references location along the stalk, with lines showing load points for node (shown at left) and internode (shown at right) tests, respectively.

FIG. 11(A) illustrates that corn has very thin walls, a foam-like parenchyma core containing vascular bundles, and a fairly thick transverse diaphragm at the node. FIG. 11(B) illustrates that reed is hollow cored, has thicker walls, and unlike corn, has a very thin transverse diaphragm at the node. FIG. 11(C) illustrates that bamboo is also hollow but has a very thick, dense node and substantially thicker walls than the other two species.

FIGS. 12A-F show experimental setups for bending and compression tests and graphs of respective responses. For FIGS. 12(A)-12(C), arrows indicate positions of loading anvils; circles indicate positions of supporting anvils. P is the value of the applied load. L is the distance between support anvils, and a is the distance from the applied load to the supporting anvil. FIG. 12(A) shows a three-point bending test setup in both the node-loaded (black) and internode-loaded (gray) configurations. FIG. 12 (B) shows a four-point bending test setup. FIG. 12 (C) shows a transverse compression test setup. FIG. 12 (D) shows a graph of bending moment along the length of the stalk for the three-point bending test setups. Three-point bending induces a maximum moment directly beneath the loading anvil. FIG. 12(E) shows a graph of bending moment along the length of the stalk for the four-point bending test setup. This test setup induces a constant moment between the two loading anvils. FIG. 12 (F) shows a graph of a typical load deformation response of samples loaded in transverse compression. Structural transverse stiffness was calculated as the average slope of the load deformation curve.

FIGS. 15 (A),15 (C), and 15(E) are node-loaded

FIG. 20 is a graph of observed data on stalk strength vs cantilevered flexural rigidity.

DETAILED DESCRIPTION OF THE PREFERRED EMBODIMENTS

Figure 1A:
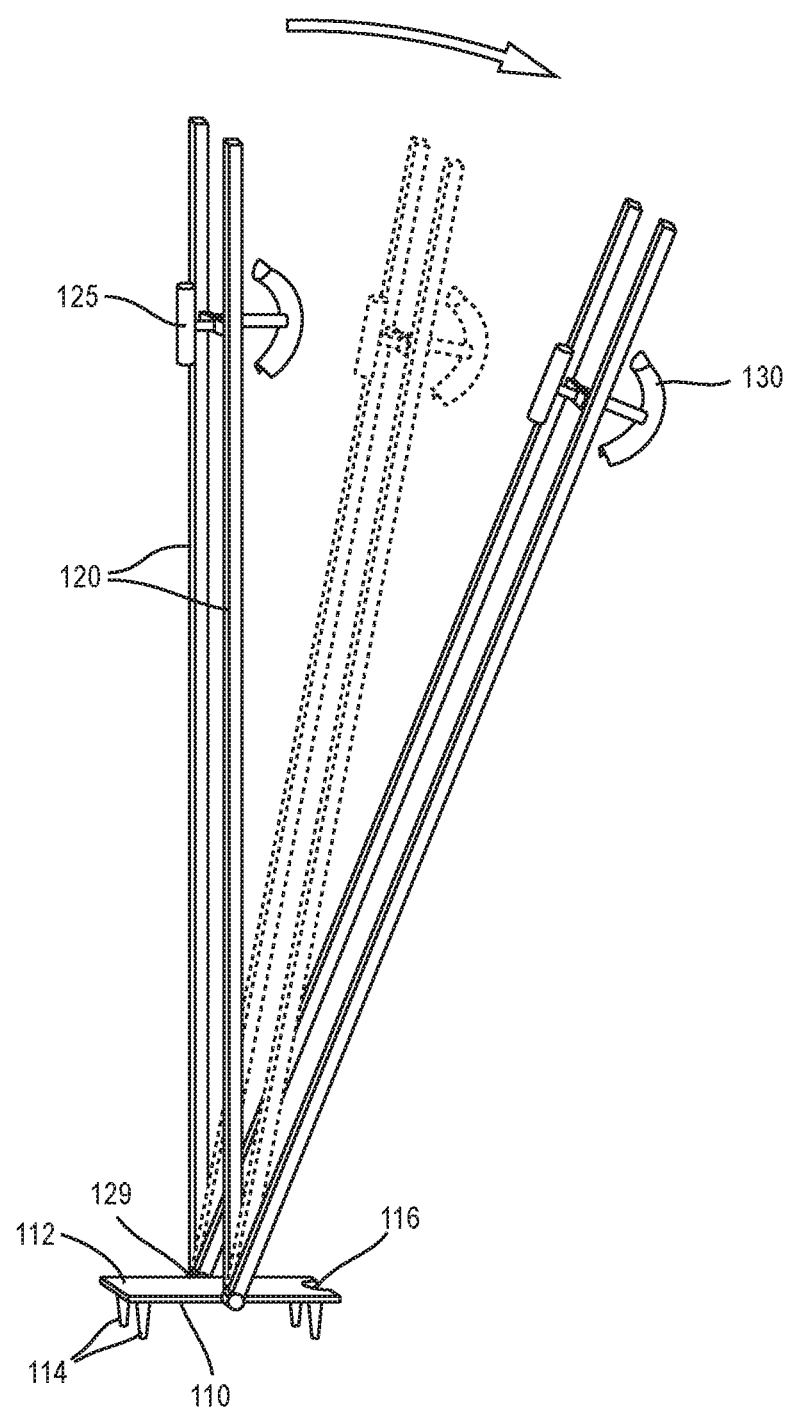
FIG. 1A illustrates a stem testing apparatus.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

The present invention relates to apparatus and methods for measuring force and displacement response of an object. One embodiment relates to systems and methods for measuring flexural rigidity. Another embodiment to the selection of plants based upon their measured flexural rigidity.

When undergoing natural wind loads in the field, corn plants may be modelled as vertical cantilever beams undergoing bending due to a distributed lateral load. In reality, corn plants undergo a significant amount of deflection before failure, causing a perpendicular force to deviate significantly from the horizontal direction applicable at small deformations. Therefore, an exact treatment of the problem would require detailed knowledge of the deflection path of corn stalks in order to maintain perpendicularity between the force and the stalk, as well as to apply the force to the same point on the stalk as deflection is increased. The deflection path of tapered, septate, hollow tubes with irregular cross-section such as corn stalks is not available in the literature. Moreover, it is expected that natural geometric and material variation between plants would preclude a meaningful description of a universal deflection path. Fortunately, flexural rigidity can determined from the elastic modulus of the structure at small deflections, allowing the deflection path to be approximated as a circle centered at a point just above where the stalk emerges from the ground. The "rotating-on strength" or flexural rigidity is robust to variations in environmental factors such as variety, planting density, planting location.

Engineering beam theory is commonly used by structural engineers to quantify the bending stiffness and strength of buildings, beams, and structures. In the current work the authors sought inspiration from the equations of engineering beam theory to develop a nondestructive means of predicting corn stem strength. It was hypothesized that stem strength could be predicted by slightly flexing stems to obtain a composite bending stiffness measurement which was termed 'stem or stalk flexural stiffness'. The measurement can be calculated as follows:

$$\text{Stalk Flexural Stiffness} = \emptyset \frac{a^2 b^2}{b}, \quad (1)$$

where Ø is the slope of the force/displacement curve obtained by slightly flexing the stalk in three point bending, a and b are the distances to the applied load as measured from the supports on the left and right sides of the stalk respectively, and L is the distance between supports. In the current study slope measurements (Ø) were obtained by inducing less than 6 mm of stalk deflection. This ensured the test did not induce any permanent damage to the stalk.

In one embodiment, an apparatus applies and measures the force and displacement response of a stem or plant (i.e. either a force is applied and displacement is measured or a displacement is applied and force is measured). In one embodiment, the measured force and displacement are at the same time, i.e. the measured force is associated with the applied displacement and vice-versa. The force may be applied perpendicular to the stem or at an angle with respect to the stem. Force displacement data is used to calculate the plant's bending stiffness or flexural rigidity. Analyses has shown that flexural rigidity (bending stiffness) is highly correlated to stem strength and is a much stronger predictor of stem strength than prior art technologies. For example in one embodiment involving corn stalks:

$$\text{Bending strength} = 1.49 E^{-4} * \text{flexural rigidity} + 1.62$$

where strength is in Newton meters and flexural rigidity is in Newton meters$^2$. It should be appreciated that alternative embodiments may utilize a different relationship of stem strength and flexural rigidity. The process of acquiring force displacement data and calculating the stems flexural rigidity does not require permanently damaging or breaking the stem. In addition, in certain embodiments bending strength for the stem can be directly measured.

It has been discovered that a rotating arm with a pivot at ground level is a feasible way of controlling the direction of the user applied force. The magnitude of the force applied to the stems can be best measured at the point of engagement between stem and device. A testing apparatus can thus be provided that is able to predict the strength of stems with a high degree of accuracy without permanently damaging the plant. The testing apparatus can be deployed in the field, does not require prepping the stem in any manner, and requires a relatively small amount of time to implement. Another embodiment might be an automated mechanism to measure the flexural rigidity of stems. For example, a support may extend from a tractor or the like and engage stems while the tractor moves along a row of crops, measuring information as described below. A single operator could then measure large numbers of plants very effectively.

In one embodiment, a testing apparatus 101 is provided. The primary mechanical elements of the testing apparatus 101 are a base 110, a support 120 movable about a hinge 129 (such as first hinged arm 121 and a second hinged arm 122), and a contact element 130 for contacting the stem of the plant being measured.

The support 120 may comprise one or more arms, for example a single pivoting arm 121 or twin pivoting arms 121, 122. FIG. 1B illustrates an embodiment with two arms 121, 122. FIG. 1C illustrates an embodiment with two arms. The support may be selected to provide sufficient rigidity to the apparatus 101. It should be appreciated that a balance of rigidity vs weight and cost is desirable. Where more than one arm 121 is present, cross-bracing or brackets connecting the two or more arms 121, 122 may be used. In one embodiment a support 120 provides sufficient support to the contact element 130 while presenting an overall reduced weight and cost.

Figure 19:
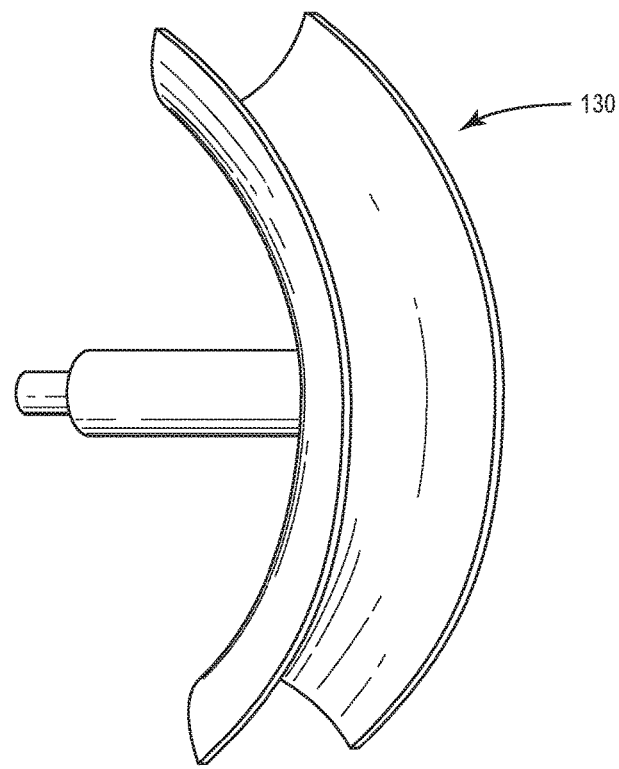
FIG. 19 illustrates a contact element having an anvil form factor.

The contact element 130 applies the force to the stem. The contact element 130 has a form factor selected for engagement with the stem. In one embodiment, the contact element 130 comprises a fixed anvil, such as a curved anvil shown in FIG. 19A. In an alternative embodiment, the contact element 130 comprises a roller. The contact element 130 is selected, and positioned relative to the support 120, to transfer force from the apparatus to the stem. In one embodiment, the contact element 130 attached to the support 120, such as movably attached to allow the contact element to be positioned along a length of the support 120. This positionability allows a user to adjust the "height" of the contact element 130, controlling the contact point on the stem. FIG. 19A shows a fixed anvil embodiment. The anvil design provides for a sliding surface to move the stem smoothly and apply a pure lateral point load. The roller embodiment provides for a rolling engagement at a lateral point with the stem. In one embodiment, the roller provides for a superior engagement with the stem. The roller minimizes the moment applied to the stem compared to the anvil. This avoids artificially low force values that can result from moments being absorbed by the linear bearing housing the stem, increasing accuracy. In one embodiment, the force applied may be sufficient to be destructive, i.e. take the plant past the breakage point, or non-destructive, insufficient to result in breakage.

Further, measurement components may be included. In particular embodiments, measurement components include one or more of a force gauge 141 (a.k.a. load cell), and a displacement sensor 142 to measure the angular displacement of the support 120, and the necessary electronic components to synchronously record angular displacement and force. The displacement sensor 142 is, in one embodiment, selected from a rotary encoder or a combination of an accelerometer and gyroscopic sensor. The force gauge 141 may directly contact the plant or may be associated with a contact element 130. The force gauge can be one of various types known in the art, including a thin-film pressure sensor, a miniature load button cell, or a S-beam load cell. Thin film pressure sensors provide for superior weight, size and cost. However, load button cells provide for more accuracy without much undue tradeoffs for weight, size and cost. A S-beam load cell can be used with the advantage of ease of attachment through a threaded interface.

The rotary encoder 142 may be located at the hinge 129. In an alternative embodiment, gyrometers and accelerometers are utilized along with or in place of the rotary encoder 142. These devices may be attached to the support 120 rather than at the hinge 129 as with the rotary encoder 142. The rotary encoder 142 may facilitate measurement of deflection by rotation-based measurement or inclination-based measurement. Measuring deflection using a rotary potentiometer is likely to cost less than an inertial measurement unit (IMU) required to measure the inclination of the arm. However, the inclination approach would allow the base 110 of the device to be eliminated, significantly decreasing size and improving maneuverability.

The testing apparatus 101 allows control of several aspects to provide various methods and systems for testing. The direction of user applied force can be controlled (pivoting arm). The force applied and how applied can be controlled by the contact element 130 (fixed anvil or live roller). Force measurement can be controlled and implemented by various structures, including force sensors. The contact element 130 and rotary encoder 142 may be in communication with a device control and/or data acquisition device.

In one embodiment, the base 110 includes a body portion 112 that is substantially flat on a bottom side for engaging the ground. One or more protrusions, such as spikes 114, may be included to provide additional structure engagement with the ground or surface upon which the base 110 rests. The body portion 112 may further include a notch, groove, or the like 116 to accept all or a portion of the plant stem. The support 120 is hingedly attached to the base 110. In one embodiment, such as FIG. 1A, the support 120 is directly hingedly attached to the base 110. In an alternative embodiment, such as FIG. 1B, the support 120 is mechanically coupled to the base 110 and moveable about a hinge 129 relative to the base 110.

The support 120 supports the contact element 130. In one embodiment, the contact element 130 is adjustably connected to the support 120, such as by a threaded connector capturing the support 120 there between. A handle 128 may be provided on the support 120, such as attached to the contact element 130, to facilitate usage. The contact element 130 pivots about the hinge 129, in one embodiment. The contact element 130 may sildably or removably engage the support 120 to allow for adjustment of the distance between the support 120 and the base 110 to accommodate different stem sizes or placement of the contact element 130 specifically with reference to a particular stem.

Several additional features could be added to increase the ease of use of the testing apparatus 101. Additional features could include a readout display, buttons for starting and stopping tests, GPS (global positioning system) data system to record the precise geographic location of each measurement. Spikes 114 could be added to the base 110 to aid in stabilizing the base 110 from motion during operation.

In one embodiment, a processor and memory are provided. One or more of the measurement components are in communication therewith for processing and storage of data. Further, the same processor and memory, or a separate processor and memory may be utilized to control the apparatus 101, such as where the apparatus 101 is automated.

Figure 18:
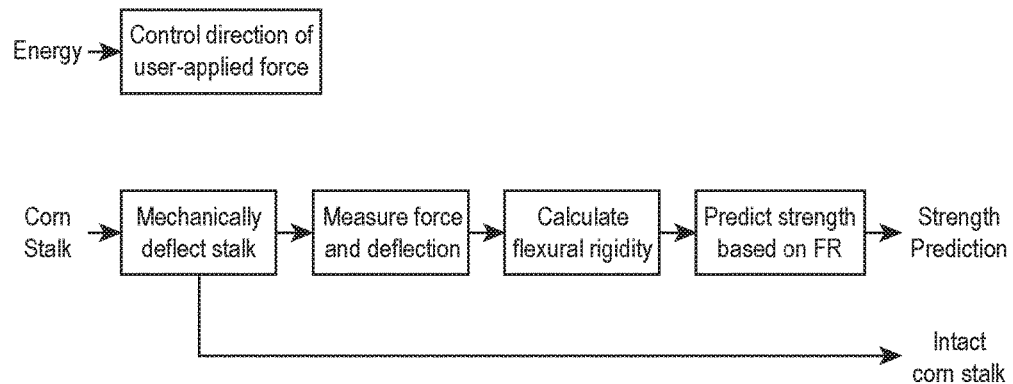
FIG. 18 illustrates a flow chart depicting one embodiment of determining flexural rigidity for a crop.

The overall function of the apparatus 101 is to carry out a cantilever bending test in the field to determine stem flexural rigidity. This processed may be decomposed into several subprocesses as illustrated in FIG. 18. First, the device has to direct the user applied force such that it remains perpendicular to the stem axis throughout the test in order to comply with assumptions inherent to the beam deflection equations used to model the stem's mechanical response. In one embodiment, the force could be applied by electromechanical device, in which case the measurement of force could be measured from the electromechanical device, such as torque on a drive shaft or applied voltage. This force will then have to be transferred to the stem to bend it while avoiding lateral crushing to prevent premature failure. Subsequently, both the force applied to the stem and the corresponding deflection have to be measured simultaneously. Finally, stem flexural rigidity needs to be calculated from this bivariate force and deflection data and fed into preexisting regression models to generate predictions on stem strength.

In one embodiment, the testing apparatus 101 is operated by setting the base 110 near the plant to be measured. The stem of the plant located in the notch 116 at the top of the base 110. To prevent the base 110 from moving, the operator places weight on the base 110 during operation. The contact element 130 is adjusted along the support 120. In one embodiment, the contact element 130 is positioned to contact a node area. As the support is moved forward, such as by rotating about the hinge 129, resulting in an angular motion of the support 120 and the contact element 130, the contacting element 130 will come into contact with the stem. After contact, the user will push the stem forward by approximately 1-20 cm. In one embodiment, this distance is calculated from data obtained by the rotational encoder 142 in combination with the height of the contact element 130. Note distance could also be measured using accelerometers and gyroscopes attached to the contact element or to the supports. Also note the user could push the stem forward by as little as 5 mm or until the stem breaks. Any displacement in this range would enable calculation of flexural rigidity. However, between 1-20 cm is believed to be the most feasible range.

During this time, the load cell 141 will take a series of force measurements and the rotary encoder 142 will simultaneously make a series of measurements of angular rotation. To calculate flexural rigidity, these measurements must be synchronized (i.e. each angular measurements must be recorded at the same time as the associated force measurement).

In one embodiment, the testing apparatus 101 is utilized by placing the contacting element immediately basal to the node line (FIGS. 5 A, 5C and 5E) and not in the middle of an internode section. The contacting element 130 should be placed such that the span length is maximized to reduce the transverse load required to achieve a bending moment on the sample. In general, span length should be greater than 20×the diameter of the stem. The contacting element 130 should be shaped so as to not damage the stem. For example, the shape of the contacting element 130 and support 120 should have no sharp corners or edges but rather be rounded (as seen in FIG. 15) to maximize contact between the sample and loading instrument, thus distributing transverse forces over a larger area of the sample.

The method of use should utilize a speed of movement of the support 120 and contacting element 130 such that the rate of defection minimizes viscoelastic effects. At very slow speeds, stress relaxation will occur, and at very fast speeds, strain hardening will occur. Crosshead speeds described in the studies below may be used for certain embodiments. For other embodiments, speed will depend on numerous factors, including test setup, species, moisture content of the sample, etc. When testing corn stem the rate at which the stem is displaced affects both flexural rigidity and strength. This is typical of most all biological tissues. Test performed at high rates of displacement resulted in higher breaking strength and higher flexural rigidity values than test performed at slow rates. For example, a device was used to break stems at "slow", "medium", and "fast" speeds.

Further, for the method to provide broadly applicable results, both nodal and internodal tissues should be flexed during any test that intends to produce results generalizable to the entire stem or stalk.

In another one embodiment, testing apparatus 101 has a contacting element 130 that is adapted to perform the same displacement each time a stem is tested. A series of data of various stalks tested with the same displacement need not measure deflection if the force applied and displacement are known. Such can then be utilized to determine a prediction of relative stem strength.

In one embodiment, the contacting element 130 causes cantilevered bending on the stem, as the stem is secured at the ground (a first point) and then contacts the contacting element 130 at a second point. That is, there is no "third point" of contact as is used in a three-point test.

In one embodiment, the testing method described herein is non-destructive to the stem. In another embodiment, an apparatus described herein can be utilized to directly determine bending strength by displacing the stem until it breaks. The failure moment is calculated and strongly correlated with stem lodging (breakage).

The apparatus 101 does not necessarily have to contact the stalk at a node line. It could also contact the stalk in the center of an internode. Since relatively small displacements are being used to calculate flexural rigidity the reduction in accuracy by contacting the stalk at an internode should be minimal.

In one embodiment the apparatus includes a force sensor and accelerometers. Height from the ground and force/displacement are tracked. The apparatus engages the stem and the related information is recorded. For example, the apparatus 101 may have the base 110, support 120, contact element 130 structure described above. In the alternative, the apparatus 101 may be a wearable device, such as a glove (not shown) with pressure sensors and accelerometers. The glove provides information regarding position above the ground, such as through use of sensors, and provides data on the displacement distance when the glove engages a stem.

Load Placement Assessment

A load placement study was performed. The purpose of this study was to investigate the effect of test configurations on the results of three-point bending tests involving corn stalks. It was hypothesized that loading configuration does affect three-point bending test results, with lower maximum loads recorded when the load is placed at the internode as compared with the node. It was further hypothesized that the application of the transverse load at the node reduces artifactual results and produces failure patterns more consistent with in-field observations. This study was performed to test these hypotheses and to develop a testing protocol that provides reliable, objective measures of corn stalk strength.

Methods

Stalk samples were drawn from four commercial varieties of dent corn and at four different planting densities. Eight sets of stalks were sampled, with five stalks in each set, for a total of 40 stalks (hybrids A and B at planting densities of 36 thousand and 48 thousand plants per acre, hybrid C at planting densities of 30 thousand and 48 thousand plants per acre, and hybrid D at 30 thousand and 42 thousand plants per acre). All stalks were harvested in Greenville, Iowa immediately before harvest. Stalks were cut just above ground level; the ear was removed along with the portion of the stalk above the ear node. To prevent spoilage, stalks were placed in a forced air dryer to reduce stalk moisture level to between 10% and 13%. All stalks were checked for disease and pest damage. Only stalks exhibiting no visible evidence of damage were included in the study.

Flexural Tests

To test the hypothesis that loading location influences failure load levels, three-point bending tests were performed with two different loading configurations: (i) the load applied at the center of the internode region and (ii) the load applied immediately below the node line.

Tests were conducted using an Instron 5965 test frame with a 500-N load cell. All stalks were oriented such that the loading direction was parallel to the minor axis of the stalk cross section. During testing, the load anvil was displaced at a rate of 10 cm $\min_{-1}$. Load and displacement data were recorded every 100 ms, just until failure of the stalk was detected. Failure was defined as the point on the force-displacement curve where load began to decrease with increasing deflection. This occurs due to irreversible damage to the structural integrity of the stalk (e.g., cell walls crushing or buckling, stalk breakage).

To facilitate comparison and reduce experimental variation, each stalk was tested in both three-point bending configurations. Node loading tests were performed first. The load was applied at a central node, with the stalk supported at the second nodes above and below the loaded node. This loading configuration consistently produced failure near the loaded node, with failure always restricted to one side of the node (i.e., failure did not propagate through the node). The non-damaged, adjacent internode was then used for subsequent internode testing. A span length of 100 mm was used for all internode tests.

Strength Comparisons—

Figure 2:
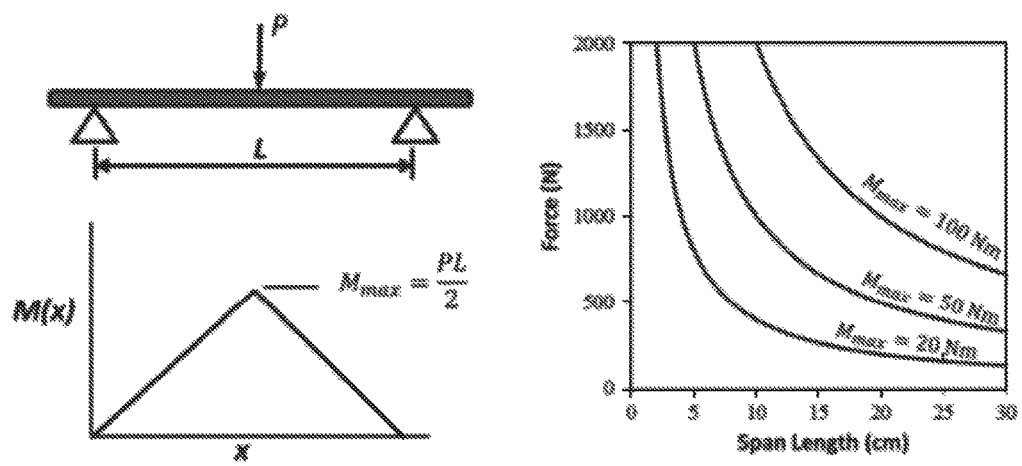
FIG. 2 Top left: Diagram depicting the loading and boundary conditions imposed during three-point bending tests where P is the applied load and L the length between supports. Bottom left: Bending moment diagram displaying the bending moment M as a function of x (length along the beam). Right: Bending moment isoclines for three-point bending tests illustrating that multiple combinations of span length and applied force can produce the same bending moment.

Bending failure is governed by the bending moment, which depends on two factors: the applied force itself and the span between the force and supports (see FIG. 2). When subjected to three-point bending, internal forces (called bending moments) act to cause bending at each cross section along the span of the structure. The bending moment at any given point along the length of the structure can be found using Eq. [1]. As shown in FIG. 2 and Eq. [1], the bending moment depends on the load, P, the span, L, and the location of interest, x. The maximum bending moment always occurs at the central loading point and has a value of $M_{max}$=PL/2. Because the bending moment depends on both force and span, the same bending moment can be achieved using a variety of force-span combinations, as illustrated in the right side of FIG. 2.

$$M(x) = \begin{cases} Px & | \quad 0 \le x \le L/2 \\ P(L-x) & | \quad L/2 \le x \le L \end{cases}$$

Bending tests were used to make two types of comparisons. First, comparisons between node-loaded and internode-loaded sections were made by direct comparison of the bending moment at failure for both tests. Although this approach provides a comparison of the moments required to cause failure, differences in the cross-sectional shape, size, rind thickness, etc. between the two tests could potentially affect the results. A more relevant and direct comparison is possible by calculating the internal bending moment that acted at the internode region during the node-loading experiments. For example, the above equation and the loading configuration of FIG. 2, one can determine that the bending moment, M, at the point x=L/4 is M=PL/4.

Therefore, the second method of comparison was to calculate the maximum bending moment applied at the internode during the node-loaded test. This quantity was then compared with the maximum bending moment applied during internode-loaded experiments. This approach accounts for all cross-sectional and size factors, providing a direct comparison by which the effect of internode loading can be evaluated.

Statistical Tests—

A statistical comparison of the means from each type of test was performed using a two-sample t test. The two-tail p-value was calculated from the resulting student t test statistic. For comparisons between bending moment applied at the internode during node-loaded and internode-loaded cases, a two-sided paired difference test was used to determine if there were statistical differences in stalk strength under node-loaded or internode-loaded cases.

Transverse Compression Tests—

In bending experiments, stresses, stiffness, and failure are all closely related to cross-sectional shape. The concentrated load applied during three-point bending experiments has the potential to deform the cross-sectional shape of the corn stalk, thus reducing bending stiffness and possibly contributing to premature failure. To assess the influence of the transverse load on stalk shape, the cross-sectional stiffness of the stalk was measured at various points along the length of the stalk.

Cross-sectional stiffness was measured using the same machine and loading fixtures as described above. Intact stalks were compressed by opposing forces, with the load applied directly above the support. The upper anvil was displaced downward, causing a compressional force. To measure stiffness without damaging the stalk, all tests were performed with a maximum deformation of 0.2 mm and a loading rate of 2 mm $min_{-1}$. Cross-sectional stiffness was determined as the average slope of the resulting force-deformation curve, and this test was repeated at intervals of 5 mm along the length of the stalk.

Results

All stalks exhibited remarkably similar behavior under each of the experiments described above. Consequently, the data below represent aggregate results based on the combination of all stalks into a single sample (n=40) consisting of four different commercial hybrids grown at four different planting densities.

Figure 3:
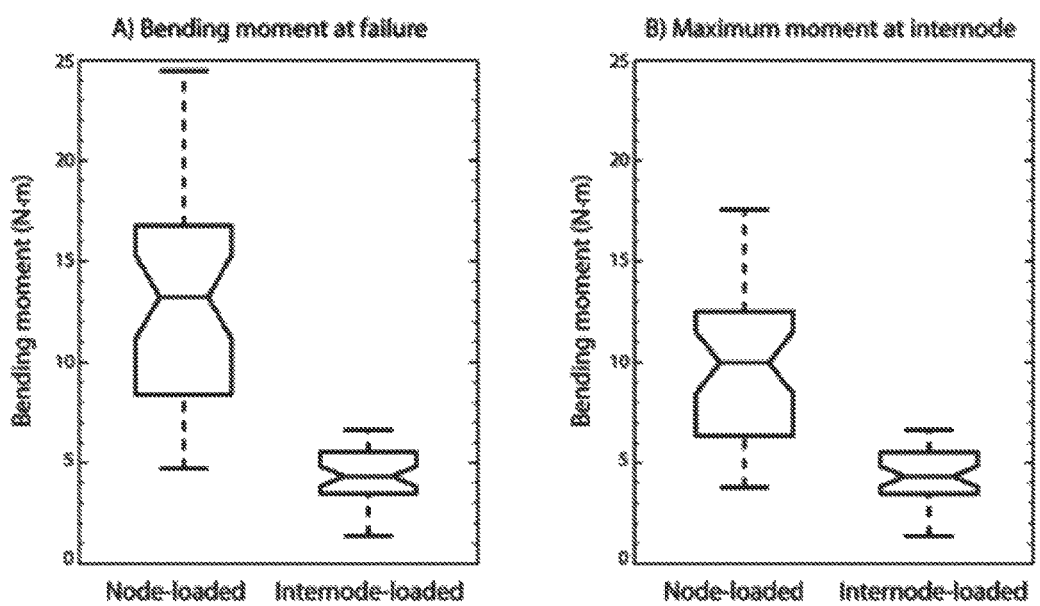
FIGS. 3A-B are box plot diagrams of bending moment comparisons between node-loaded and internode-loaded three-point bending tests of corn stalk.

Differences between node-loaded and internode-loaded tests are depicted in FIGS. 3a and 3b using box plots of the bending moment at failure for both the node and internode tests. Results show that stalks that were loaded at the internodes failed at significantly lower moments than when loaded at the nodes (p<0.001). A second, more direct comparison of moments is made in FIG. 3b. As discussed above, this comparison is based on the maximum bending moments applied to the center of the same internode during the node-loaded and internode-loaded tests. FIG. 3b shows that a much higher bending moment was experienced at the internode during the node-loaded test than was required to fail the same section during the internode-loaded test. On average, when loaded at the internode, stalks failed at a bending moment that was 54% lower than the bending moment applied at the same point during the node-loaded tests. Paired t tests were performed for each set of five stalks and for the entire set of 40 stalks. For individual sets of five stalks, all were statistically significant, with the largest p-value obtained being p=0.015. For the combined set of 40 stalks, the result was highly significant, $p=1.0 \times 10_{-13}$.

It is important to note that failure did not occur at the internode during the node-loaded test. In other words, every internode in this study withstood a higher bending moment during the node-loading test than the moment that caused failure during the internode test. Because node-loaded data of FIG. 3b represents unfailed stalks, while the internode-loaded data represents failed stalks, the reported 54% reduction in failure moment should be interpreted as a minimum estimate for the difference induced by loading at the internode.

All stalks exhibited similar cross-sectional stiffness patterns in which the internode region was less stiff than nodal regions. Transverse compressive stiffness versus distance along the stalk is given for a representative corn stalk in FIG. 4. An X-ray image of the same stalk is shown at the bottom of the figure for anatomical reference. The distinct, periodic peaks in stiffness observed in FIG. 4 are a consequence of the morphological and anatomical structure of corn stalk. In particular, peaks in stiffness coincide with each node, which is shown as the darker tissue in the X-ray image. Not only does the stalk diameter increase in nodal regions but rind thickness and tissue density increase as well (see X-ray image). These differences in nodal tissues substantially increase the node's ability to support transverse loads. In fact, comparison of the stiffness values calculated at the node and the center of each internode indicate that nodes are more than twice as stiff as internodes (one-tail t test, p<0.001). As such, nodes are a prime location to place the loading anvil of three-point bending experiments because they are far more resistant to localized cross-sectional deformation.

Figure 6:
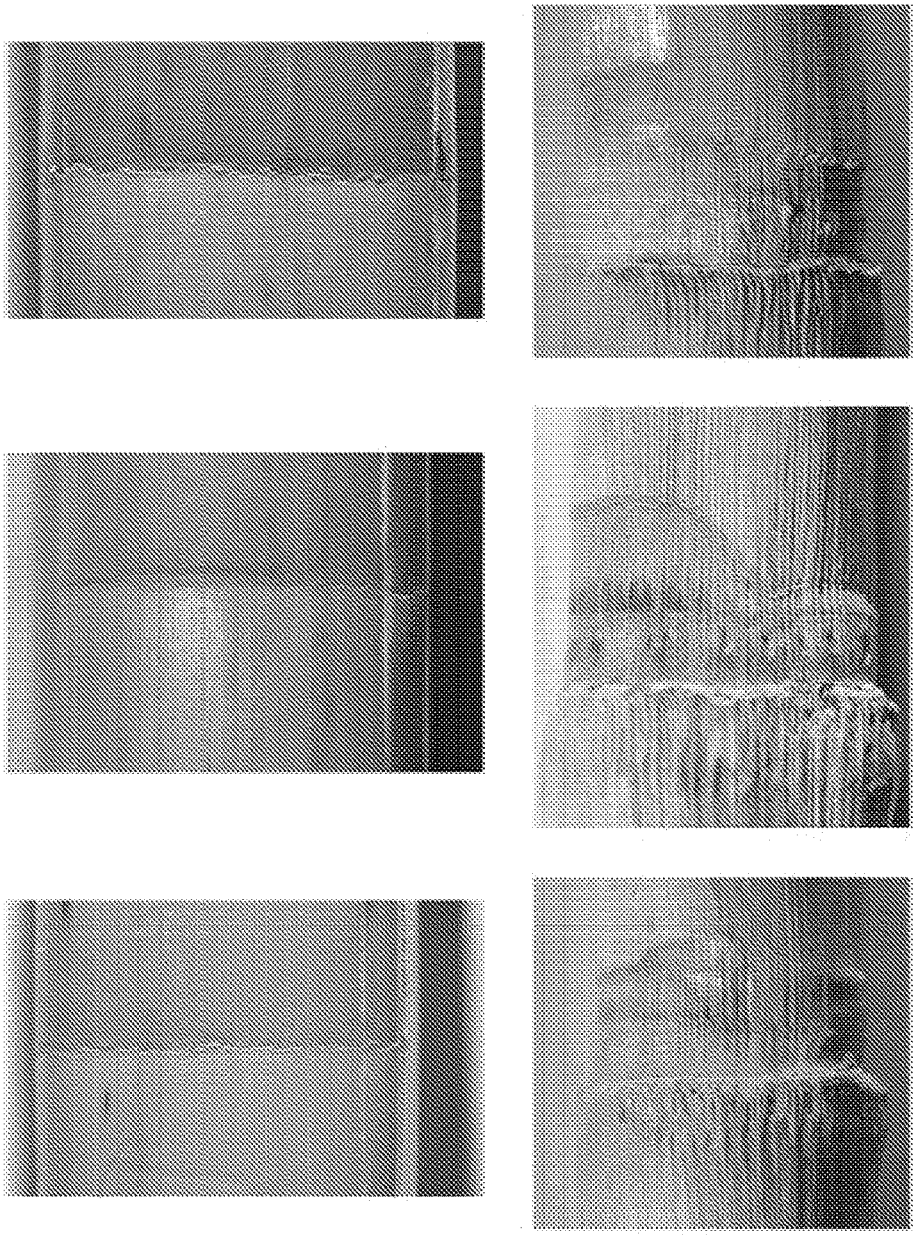
FIG. 6 shows Images of general failure types and locations for internode (top) and node (bottom) loaded three-point bending tests of corn stalk.

FIG. 5 depicts the failure locations of internode-loaded stalks and node-loaded stalks. Representative pictures of the type of failures are displayed in FIG. 6. It was found that all internode-loaded stalks failed in the same location and in the same manner: a single creased line located at the point where the loading anvil contacted the stalk. This pattern of failure is not similar to observations of in-field failures. Stalks failed under natural loading conditions typically display variation in both type and location of failure. Results from node-loaded three-point bending tests agreed well with in-field failure observations: they demonstrated variability in location, type, and path of tissue failure across the stalk (see FIG. 6). For node-loaded stalks, failure occurred away from the loading anvil and just above the node, with slight variations in the exact location of failure. In addition, failure crease patterns of node-loaded test specimens were unique for each stalk. These results suggest natural variation in the location and type of failure when loaded at the node.

Figure 7A:
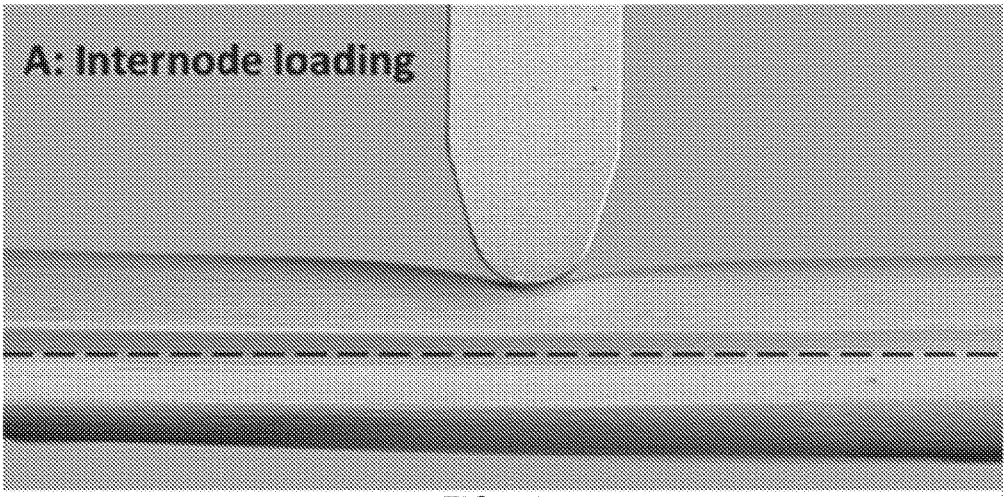
FIG. 7. Images of corn stalk captured immediately before failure, illustrating differences in deformation patterns. (A) Internode loading, (B) node loading. A horizontal line is provided as a reference in each image.
Figure 7B:
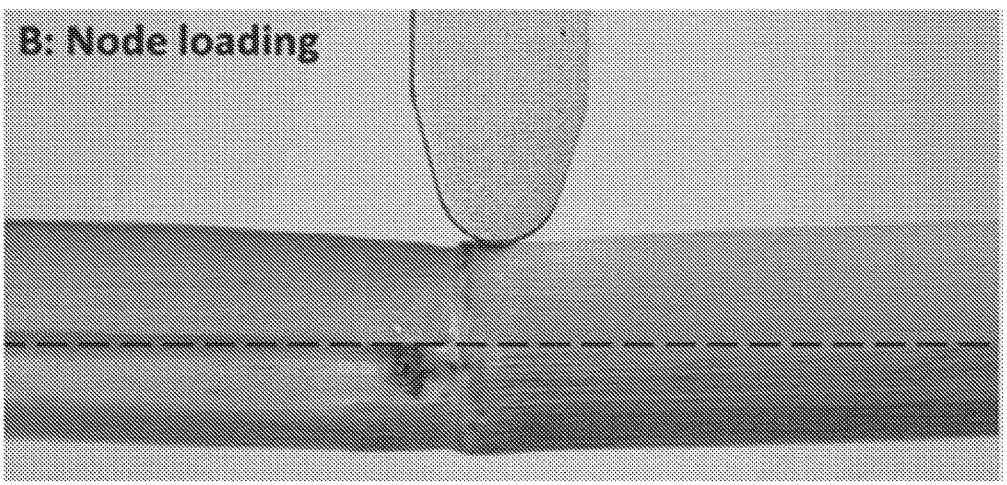

FIG. 7 displays photographs of node-loaded and internode-loaded corn samples immediately before failure. Significant transverse deformation was apparent at and around the loading anvil before failure in all internode-loaded samples, as shown in FIG. 7A. During internode-loaded tests, cross-sectional deformation at the load location occurred almost immediately on contact of the loading anvil with the stalk. In contrast, node-loaded stalks (FIG. 7B) exhibited obvious bending deformation, but no visible transverse compression of the stalk.

Discussion

Deformation and Failure of Thin-Walled Stalks—

Under three-point bending, a transverse load is applied as a means of imposing a bending moment on the specimen. This transverse load has two effects on the stalk, regardless of loading location. The first is intentional: to cause a bending moment, which acts to bend the stalk (FIG. 2). The second is an unintentional consequence of the first: the load imposes transverse compression on the stalk (see FIGS. 4 and 6). The manner in which bending and transverse compression affects the stalk was observed to depend on the point of load application.

When a load is placed at the internode region, transverse deformation (FIG. 7A) is significant, and bending deformation is often minimal. This is due to the relatively low transverse stiffness of the internode region (FIG. 4). Deformation of the cross-section reduces the stalk's ability to resist bending stresses and causes it to be especially susceptible to buckling failure. Eventually, the concentrated load of the anvil, combined with the relatively low transverse stiffness of the stalk, cause creasing of the stalk at the point of loading. A nearly straight crease propagates along the stalk rind, leading to the failure patterns shown in the top row of FIG. 6 and the red data of FIG. 5. For internode-loading, compressional stresses appear to be the dominant cause of failure. The lack of variation in failure pattern and location indicate that such failure is a result of interactions between the stalk and the test instrument. Under node loading, the internode region supported an average bending moment of approximately 10 Nm without failure. In contrast, the same region failed under an average bending moment of just 4 Nm when the load was placed at the internode.

Transverse and bending deformation also both occur when the load is placed at the node. However, the high transverse stiffness at the node (FIG. 4) results in negligible transverse compression at the node (FIG. 7B). As the load increases, bending deformation therefore dominates, and bending stresses eventually cause failure near (but not at) the loading point. Failures of node-loaded stalks vary in both failure pattern and location (FIGS. 5 and 6), suggesting that these failures are determined by local irregularities and/or weaknesses in the stalk.

The Influence of Span Length—

Span length affects the force levels of three-point bending tests. There are a number of load-span combinations that can be used to achieve any bending moment. As the span increases, the force required to achieve a prescribed moment decreases (and vice versa), as shown in FIG. 2. Even though the node is stiffer and stronger than the internode under transverse compression, it is not indestructible. During other experiments in the laboratory, node regions have been crushed in transverse compression when the span length is quite short. Thus, in addition to the loading point, the span length of three-point bending tests should be considered when designing three-point bending tests. In general, in one embodiment the span length is maximized to minimize the transverse load.

Limitations—

While this study was based on maize, it is anticipated that these results can also be extended to species having a similar structure, such as reeds and other grains. The stalks tested in this study were all collected immediately before harvest and were dried to prevent spoilage. While the drying process might have affected the precise values of the tests, it is not believed that the conclusions would be affected because the change in moisture level between harvest and drying is relatively small (~5-10%).

In addition, the drying process does not affect the overall structure of the stalk, which is characterized by stiff nodes and internode regions, which are less stiff. On the other hand, the present measurements may not be extendable to green or wet stalks. While such stalks might be expected to be stiffer at the nodes, turgor pressure might act in such a way as to make nodes and internode regions equally resistant to transverse loading.

In one embodiment, the ratio of rind thickness to stalk diameter is considered. As this ratio varies, the effects of transverse compression can be expected to change; stalks having a very thick rind (relative to the diameter) may be expected to be less susceptible to the internodal failure patterns shown above.

Conclusions

This study has provided insight into the failure mechanisms of corn stalks under three-point bending. Transverse compressional stiffness varies substantially along such stems and that the results of three-point bending tests can be influenced by the choice of loading location. Transverse loads were shown to cause substantial deformation of the stem cross section during internode-loaded tests. This deformation causes premature failure, resulting in (i) failure patterns that are unlike those observed in the field and (ii) measured moments that are artificially low.

While transverse deformation cannot be eliminated in three-point bending tests, its effects can be mitigated in two ways. First, it is preferred that loads be placed at nodal locations, which are much less susceptible to cross-sectional compression than the internode regions. Second, it is recommended that the span length be maximized for bending tests as a means of reducing transverse loads. Consideration of these factors can be used by researchers to design three-point bending tests that provide accurate, reliable measurements of corn stalk stiffness and strength. Node-loaded stalks' failure patterns were observed to more closely resemble naturally occurring failure patterns and locations than other commonly used test methods (i.e., crush tests, rind penetrometry, four-point bending, etc.). As such, node-loaded three-point bending tests are likely to provide improved phenotyping accuracy in selective breeding studies seeking to increase stalk strength and lodging resistance.

Stalk Strength Assessment

Yield losses in maize due to stalk lodging (breakage of the stalk below the ear) range from 5 to 20% annually worldwide. These losses negatively impact farmers and effect society as whole by creating instability in the overall crop supply. Selective breeding approaches to improving lodging resistance have historically relied on counting the number of lodged plants at harvest. Unfortunately, this approach is severely confounded by several uncontrolled environmental factors including, insect damage, disease, and weather patterns conducive to lodging (e.g. wind and rain storms). For example, a severe wind storm may flatten an entire field of maize regardless of the lodging resistance of stalks within the field, while the absence of wind and rain storms may leave the entire field standing regardless of the lodging resistance of any individual stalk, thus making it impossible to distinguish stronger varieties from weaker varieties. More rapid gains in lodging resistance could be achieved by developing testing methodologies that can predict lodging resistance in the absence of lodging related weather events. The purpose of the current study is to investigate a testing methodology that does not rely upon lodging related weather events and could potentially be used as a selective breeding tool to combat stalk lodging in the future.

Regardless of weather, environment, chemical composition, or stalk morphology, the culminating event in stalk lodging is structural failure (i.e. breakage) of the stalk. The majority of stalk lodging research has therefore focused on measuring and increasing stalk strength (i.e. a stronger stalk is more resistant to lodging than a weaker stalk, regardless of morphology, chemical composition or weather). However, corn stalk is a multi-scale, anisotropic, nonlinear, nonprismatic, biological structure that is subject to large deformations prior to breaking. Correctly measuring failure properties of such structures and tissues is notoriously difficult and typically requires specialized engineering expertise. However, the majority of prior studies investigating stalk lodging have naturally been performed by plant scientists who do not possess a working knowledge of advanced failure and material theory. These scientists have made valuable contributions to the field and advanced an understanding of stalk lodging. However, past studies have generally used inappropriate techniques for quantifying stalk bending strength which violate mechanical measurement principles. In particular, previous methods have generally induced premature stalk failure and produce failure types and patterns that are unrelated to the failure types and patterns of naturally lodged corn stalk. Furthermore these methods are typically time consuming, load the stalk in an unnatural manner, require specialized laboratory equipment, and employ destructive testing methodologies (physically break or crush the stalk). Consequently, after more than a century of research the confounded approach of counting lodged stalks at harvest is still the primary method used to quantify lodging resistance in selective breeding trials.

An ideal breeding tool for combating stalk lodging should 1) accurately predict stalk strength, 2) not be confounded by environmental factors (i.e. be universal in its application), 3) require minimal effort and time to use and 4) not permanently damage the stalk, thus allowing analysis of individual plants throughout their lifecycle (i.e. collection of temporal data). The consensus among many researchers is that rind puncture resistance (RPR) best adheres to the above mentioned requirements. RPR is measured by forcing a small needle or spike through the stalk and measuring the maximum applied force. The method is very fast allowing breeders to phenotype hundreds of plants in a minimal amount of time. Furthermore, it does not require breaking the stalk or killing the plant thus enabling collection of temporal data. Numerous studies have demonstrated that RPR significantly negatively correlates with stalk lodging in the field. However, despite much research RPR is still severely limited in its potential. For example, RPR can readily identify weak varieties but is generally not able to distinguish strong varieties from exceptionally superior varieties. Its utility in late stage breeding trials is therefore severely hindered. Consequently, development of ultra-high yielding crop varieties that demonstrate superior lodging resistance while being tolerant of high planting densities remains unrealized.

One embodiment provides a system and method for an alternative approach to predicting stalk strength that could be used as a breeding tool in the future to develop superior crop varieties. In particular, flexural rigidity may be used as accurate predictor of stalk strength in late stage breeding trials. Flexural rigidity (FR) is an engineering measurement used to characterize the resistance of engineering structures to bending. FR measurements can be obtained rapidly without damaging the stalk and are known from engineering theory to be strongly related to structural strength.

In one embodiment, a flexural rigidity measurement apparatus, such as apparatus 101 described above, is utilized to test and screen plants for flexural rigidity. A method of screening for selective breeding comprises measuring plants for flexural rigidity and selecting those with a flexural rigidity above a threshold for replanting, cloning, reproduction, or to serve as the source material for genetic modification.

Examples

The bending strength, flexural rigidity (FP), and rind puncture resistance (RPR) of two replicates of five commercial varieties of dent corn sown at five planting densities, in two locations, were measured and compared. RPR measurements were acquired to provide a benchmark against which to compare FR predictions. All tests were conducted in a controlled laboratory setting to limit sources of experimental noise. Future research will focus on developing field based tools and techniques to measure FR.

Plant Materials

Five commercial varieties of dent corn were grown during the 2013 season at Monsanto testing facilities in Iowa in a completely randomized block design which included five planting densities (48 k, 42 k, 36 k, 30 k and 24 k plants/ha) two locations and two replicates.

Plants were allowed to reach full maturity, and remained in the field until just before harvest. At this time ten consecutive stalks from the middle of each plot were cut just above ground level and just above the ear. Ear and leaves were removed and stalks were placed on forced air dryers to reduce moisture to approximately 13%, thus reducing the chance of spoilage. Only stalks that were found to be free of disease and pest damage were included in the current study.

Bending Strength—

Bending strength was measured using three-point bending, following the guidelines outlined in prior studies. Supports were placed at the initial and terminal nodes of each stalk sample, and the load was applied to the node closest to the center of the stalk. This approach minimizes artificial deformation of the stalk's cross-section and produces failure patterns in agreement with those observed in naturally failed specimens.

Three-point bending tests were performed using an Instron universal testing machine (Model 5965, Instron Corp., Norwood, Mass., USA). A 500-N load cell was used to collect force data every 100 ms, and the load was applied at a constant rate of 10 cm/min until breakage of the stalk occurred. Bluehill software (Instron, Norwood, Mass., USA) was used to collect force and deformation data during the test procedure. Force and displacement data were used to calculate the induced bending moment (M) according to the following equations for non-symmetric three-point bending $$M(x) = \frac{Fbx}{L}, \quad x \leq a$$
$$M(x) = \frac{Fa}{L}(L-x), \quad x > a$$

where X is the distance along the beam measured from its left side, a and b are the distances to the applied load as measured from the supports on the left and right sides of the beam respectively, L is the distance between supports (i.e. a+b) and F is the applied load. Bending strength was defined as the maximum moment applied to the stalk at the location of stalk failure.

Flexural Rigidity—

FR is commonly used by structural engineers to quantify the bending stiffness of beams. FR is equal to Young's modulus (E) times the beam's second moment of area (I). Calculation of FR for corn stalk is complicated as both E and I vary along the length of each stalk. Consequently, the current study calculated a composite value of FR for each stalk. For stalks loaded in three-point bending the composite FR of the stalk can be calculated as follows:

$$FR = \emptyset \frac{a^2 b^2}{2L},$$

where $\emptyset$ is the slope of the force/displacement curve obtained from the three-point bending test. Slope measurements were obtained by applying a minimal amount of deflection to the stalk (5 mm) to ensure the test setup did not induce any permanent damage to the stalk. Note, it should be appreciated a different formula would be used for cantilevered bending, such as by squaring the length variable rather than cubing.

Flexural rigidity can also be calculated from other bending tests. For example, in a cantilever bending test $$FR = \emptyset L^2$$

Where $\emptyset$ is the slope of the force deformation curve of a cantilevered test and L is the length from the fixed end of the beam to the applied load. It should also be appreciated that small alterations of the preceding formulas could be used to predict strength. For example squaring the length variable rather than cubing.

Rind Penetrometer Resistance (RPR)

To eliminate both intra and inter-user variation in RPR results measurements were taken in a laboratory setting, using the universal testing machine described above. This setup ensured a constant insertion angle and insertion velocity of the impinging needle. During each test the stalk was placed on a flat horizontal surface and oriented such that the minor axis of the stalk cross-section was facing up. The middle section of third above ground internode of each stalk was then punctured by a steel needle at a constant rate of 30 mm/sec. The needle was displaced until it had completely punctured the rind and entered the pith tissues. A force gauge attached to the needle measured the force of contact between the stalk and the needle. The needle was 1.5 mm in diameter and tapered to a sharp point over a distance of 5 mm. As in previous studies, RPR was defined as the maximum load achieved during each test.

Statistics—

Regression techniques were employed to assess and compare the effectiveness of FR and RPR as predictors of stalk strength. As a first assessment, measurements from all hybrids, planting densities, locations, and replicates were combined. A univariate regression was performed with both FR and RPR as independent variables and stalk strength as the dependent variable (i.e. strength vs. FR and strength vs. RPR). Coefficient of determination ($R_2$) and associated p-values were calculated for both regression lines.

To assess how relationships between strength and RPR/FR are affected by experimental factors data was grouped according to each experimental factor or covariate investigated in the current study and regression was performed. Experimental factors (i.e. covariates) investigated included, 5 hybrid types, 5 planting densities, 2 location and 2 replicates. This analysis resulted in 16 regression relationships (5 hybrids+5 planting densities+2 locations+2 replicates at each of 2 locations=16). $R_2$ values, p-values and regression line coefficients were computed for each regression.

A third analysis was conducted to determine the consistency or robustness of regression relationships for RPR and FR. This was accomplished by parsing the experimental data into training sets and validation sets. The 16 regression relationships described in the preceding paragraph were used as training sets. The corresponding validation data consisted of all the remaining experimental data. For example, with hybrid 1 data as the training set, the validation set consisted of data from hybrids 2-5, for a 20%/80% split between training and validation data. This analysis demonstrates wither or not RPR or FR data can be used to predict strength of different levels of the same covariate (i.e. can the regression model obtained from one hybrid be used to predict the strength of other hybrids, or can the relationship between FR and strength obtained at one planting density be used to predict the strength of stalks grown at other planting densities?). For each training & validation data set, a coefficient of determination was calculated between the regression line of the training set and the data of the validation set. This coefficient of determination ($R_{2valid}$) was used to assess the predictive power of each method (RPR and FR) for each covariate level. As before, this resulted in 16 training/validation set comparisons. To avoid any ambiguity, the coefficient of determination of training set data is referred to as ($R_2$) while the coefficient of determination between the regression line of the training set and the data of the validation set is referred to as ($R_{2valid}$).

Results

Good agreement between laboratory bending strength measurements and natural stalk lodging data was achieved in this study. Consistent with field data, 98% of all stalks broke due to a creasing type failure, and 95% of all failures occurred within 3 cm of a node. In addition, artificial deformation of the stalk cross-sections was not observed during any bending tests.

Univariate Regression Analysis—

Figure 8:
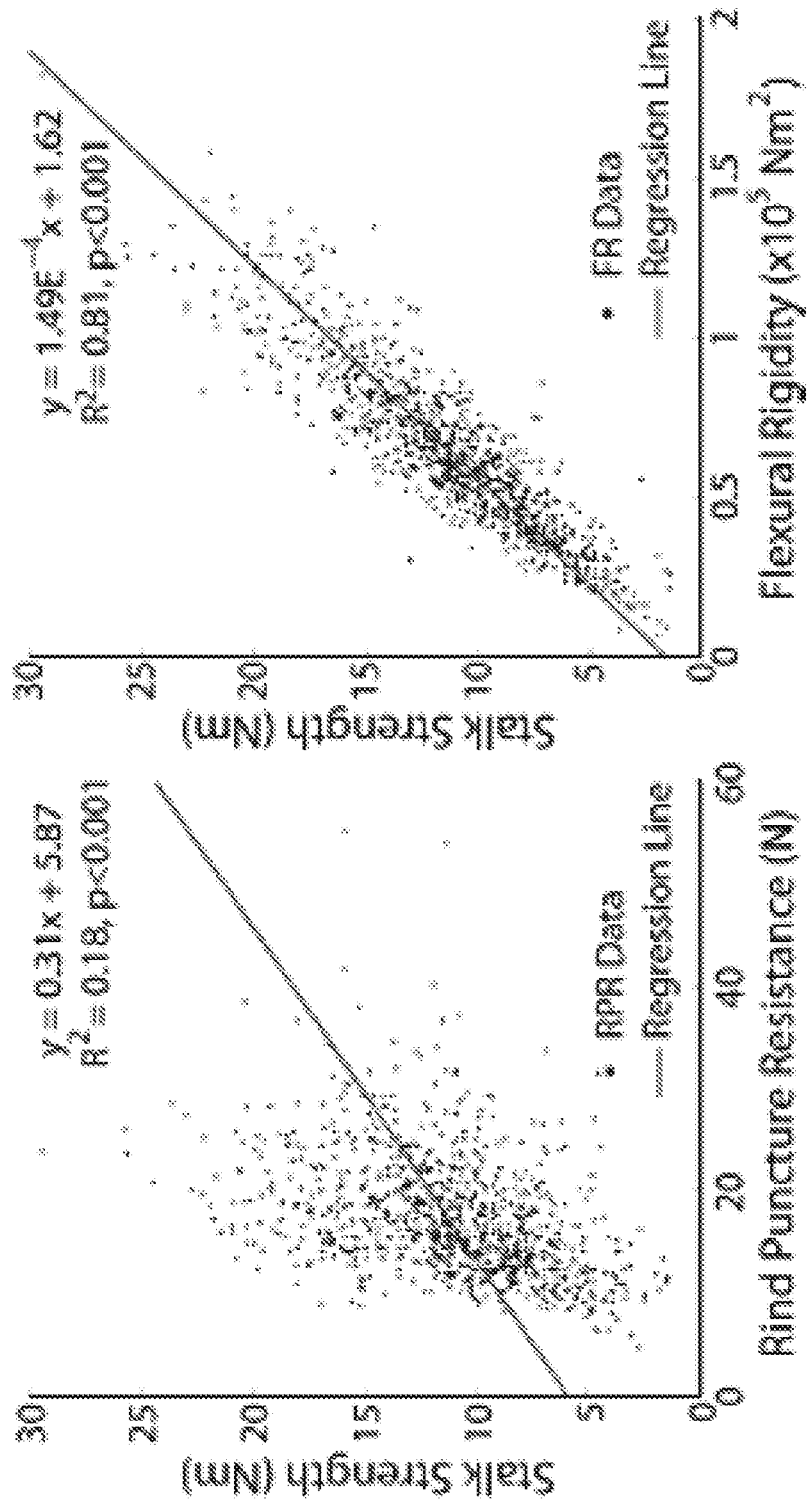
FIG. 8. Scatterplots, linear regression, and coefficients of determination ($R_2$) for correlation analysis between strength and RPR (left) and FR (right).

Univariate regression analysis revealed that both RPR and FR are correlated with stalk strength. However, FR was a much stronger predictor of stalk bending strength than RPR. Only 18% of the variation in stalk strength was predicted by RPR while FR predicted 81% of the variation in stalk strength. Furthermore, FR accurately predicted stalk strength across the entire range of measured FR values whereas the accuracy of RPR varied considerably with RPR value. Scatterplots, coefficients of determination ($R_2$), p-values, and the resulting lines of linear best fit for RPR vs. strength and FR vs. strength are provided in FIG. 8.

How were Regression Lines Affected by Experimental Factors—

Analysis of regression lines computed from grouping data according to covariate revealed that RPR was a worse predictor of stalk strength than FR. The analysis also showed that RPR predictions were significantly affected by experimental factors whereas flexural rigidity predictions were fairly consistent across all experimental factors. In particular, $R_2$ values for RPR ranged from a minimum of 0.04 to a maximum of 0.32 with a mean value of 0.19. In contrast, the minimum $R_2$ value for flexural rigidity was 0.63, with a maximum of 0.87 and a mean of 0.81. In other words, the worst flexural rigidity relationship predicted twice as much variation in stalk strength as the best RPR relationship. Regression line coefficients for RPR were also observed to vary between groups whereas regression line coefficients for FR remained fairly constant between groups. Scatter plots and regression lines computed from each level of each experimental factor investigated in this study are presented in FIG. 9. $R_2$ values and regression line coefficients are presented in Table 1.

Figure 9:
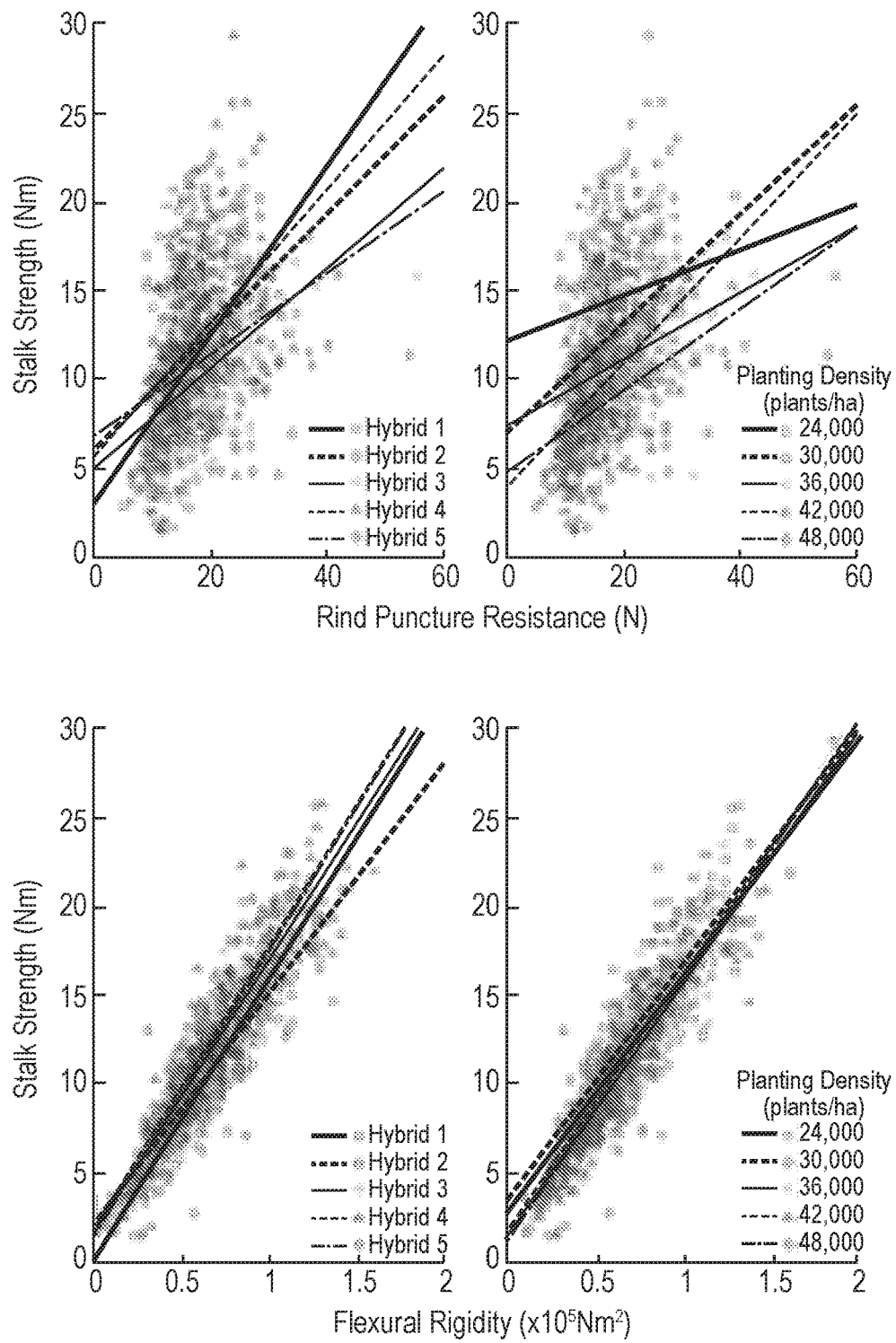
FIG. 9. Regression lines of FR and RPR vs stalk strength. RPR data shown at top and FR data shown at bottom. Data is grouped according to hybrid (left), planting density (left center), location (right center) and replicate (right).
Figure 9:
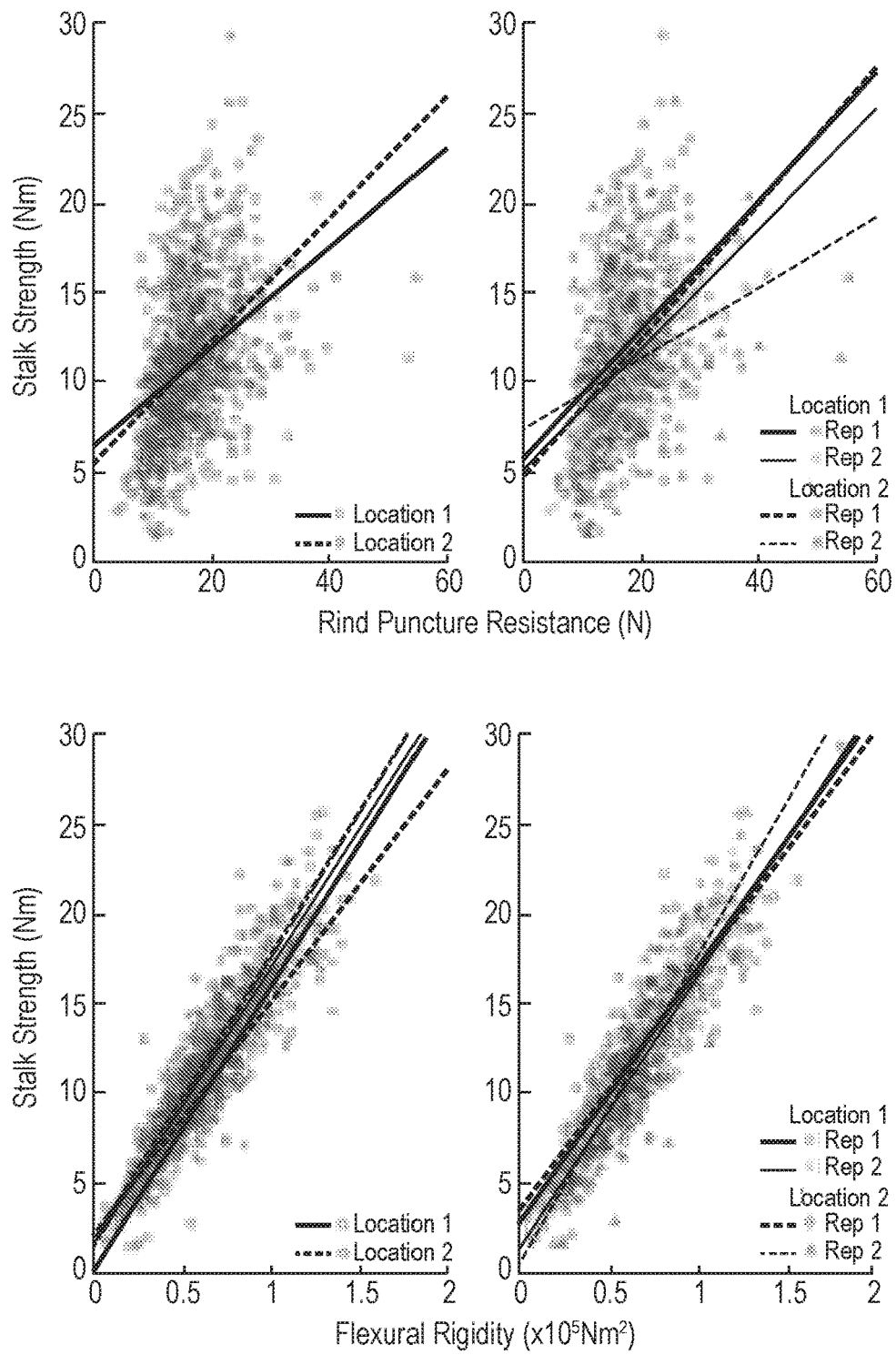

FIG. 9. Regression lines of FR and RPR vs stalk strength. RPR data shown at top and FR data shown at bottom. Data is grouped according to hybrid (left), planting density (left center), location (right center) and replicate (right).

Predictive Capabilities (Robustness) of Regressions—

The predictive potential of FR and RPR was assessed by calculating the coefficient of determination ($R_{2valid}$) between the regression lines of training data sets and the data from validation data sets. The analysis demonstrated that FR was much better at predicting strength values of validation data sets than was RPR. For example, the regression between RPR and stalk strength of hybrid 1 (training set) accounted for 32% of the variation in stalk strength ($R_2$=0.32). However, using the regression relationship from hybrid 1 to predict strength values of hybrids 2-5 based on their measured RPR values only predicts 7% of the variation in strength of Hybrids 2-5 ($R_{2valid}$=0.07). In contrast, the $R_2$ value for FR of hybrid 1 was 0.87, while $R_{2valid}$ for hybrid 1 was 0.76. Rather than an isolated anomaly, the ability of FR to predict outside its own data set was consistent across all factors and levels. This was not the case for RPR, which exhibited a substantially lower and more variable capacity for prediction outside of the training data set. These trends are evident by examining the descriptive statistics provided in the lower section of Table 2. For RPR, $R_{2valid}$ ranged from -1.0 to 0.23 with a median value of 0.12. Flexural rigidity demonstrated very different pattern, with $R_{2valid}$ values ranging from 0.74 to 0.83, indicating that flexural rigidity is well-suited for assessing stalk strength, even when using data based on different hybrids, planting densities, etc. Relative differences between $R_2$ and $R_{2valid}$ are also provided in Table 2, showing that the relative difference for RPR data was substantially higher and more variable than the relative differences for FR.

TABLE 1

Regression statistics from each level of each experimental variable investigated in the study. Summary statistics are provided at the bottom of the table. The percentage difference between $R_2$ and $R_{2valid}$ values is indicated in the "% Diff" column.

| | Rind Puncture Resistance | | | | | Flexural Rigidity | | | | |
|---|---|---|---|---|---|---|---|---|---|---|
| | Slope | γ-intercept | $R^2$ | $R_{valid}^2$ | % Diff | Slope | γ-intercept | $R^2$ | $R_{valid}^2$ | % Diff |
| Hybrid 1 | 0.48 | 3.02 | 0.32 | 0.07 | -79% | 1.58E-04 | 0.31 | 0.87 | 0.76 | -13% |
| Hybrid 2 | 0.33 | 6.29 | 0.15 | 0.13 | -14% | 1.29E-04 | 2.30 | 0.84 | 0.76 | -9% |
| Hybrid 3 | 0.28 | 4.86 | 0.28 | 0.01 | -97% | 1.56E-04 | 1.38 | 0.80 | 0.81 | 1% |
| Hybrid 4 | 0.37 | 5.82 | 0.17 | 0.05 | -68% | 1.62E-04 | 1.62 | 0.84 | 0.74 | -12% |
| Hybrid 5 | 0.23 | 6.85 | 0.15 | 0.16 | 7% | 1.63E-04 | 1.22 | 0.80 | 0.79 | -1% |
| 24k plants/ha | 0.10 | 12.21 | 0.04 | -1.01 | -2969% | 1.30E-04 | 3.64 | 0.63 | 0.75 | 18% |
| 30k plants/ha | 0.23 | 7.06 | 0.17 | 0.07 | -56% | 1.39E-04 | 2.66 | 0.79 | 0.80 | 1% |
| 36k plants/ha | 0.13 | 7.63 | 0.09 | 0.13 | 49% | 1.44E-04 | 1.85 | 0.77 | 0.82 | 7% |
| 42k plants/ha | 0.26 | 4.28 | 0.24 | 0.04 | -82% | 1.50E-04 | 1.28 | 0.84 | 0.80 | -6% |
| 48k plants/ha | 0.21 | 4.21 | 0.28 | -0.39 | -239% | 1.45E-04 | 1.40 | 0.78 | 0.77 | -1% |
| Location 1 | 0.28 | 6.20 | 0.13 | 0.23 | 80% | 1.58E-04 | 0.31 | 0.87 | 0.83 | -5% |
| Location 2 | 0.35 | 5.28 | 0.25 | 0.12 | -53% | 1.29E-04 | 2.30 | 0.84 | 0.80 | -6% |
| Rep 1, Location 1 | 0.37 | 5.44 | 0.26 | 0.12 | -54% | 1.46E-04 | 1.80 | 0.81 | 0.81 | 0% |
| Rep 2, Location 1 | 0.34 | 5.07 | 0.28 | 0.16 | -45% | 1.47E-04 | 1.91 | 0.86 | 0.80 | -7% |
| Rep 1, Location 2 | 0.38 | 4.57 | 0.18 | 0.16 | -10% | 1.39E-04 | 2.12 | 0.82 | 0.81 | -1% |
| Rep 2, Location 2 | 0.20 | 7.19 | 0.09 | 0.17 | 84% | 1.73E-04 | -0.04 | 0.80 | 0.79 | -2% |
| Min | 0.10 | 3.02 | 0.04 | -1.01 | -2969% | 1.29E-04 | -0.04 | 0.63 | 0.74 | -13% |
| Median | 0.28 | 5.63 | 0.18 | 0.12 | -54% | 1.47E-04 | 1.71 | 0.81 | 0.80 | -2% |
| Mean | 0.28 | 6.00 | 0.19 | 0.01 | -222% | 1.48E-04 | 1.63 | 0.81 | 0.79 | -2% |

TABLE 1-continued

Regression statistics from each level of each experimental variable investigated in the study. Summary statistics are provided at the bottom of the table. The percentage difference between $R_2$ and $R_{2valid}$ values is indicated in the "% Diff" column.

| | Rind Puncture Resistance | | | | | Flexural Rigidity | | | | |
|---|---|---|---|---|---|---|---|---|---|---|
| | Slope | γ-intercept | $R^2$ | $R_{valid}^2$ | % Diff | Slope | γ-intercept | $R^2$ | $R_{valid}^2$ | % Diff |
| Stdev | 0.10 | 2.08 | 0.08 | 0.31 | 737% | 1.29E−06 | 0.93 | 0.06 | 0.03 | 7% |
| Max | 0.48 | 12.21 | 0.32 | 0.23 | 84% | 1.73E−04 | 3.64 | 0.87 | 0.83 | 18% |

Figure 10:
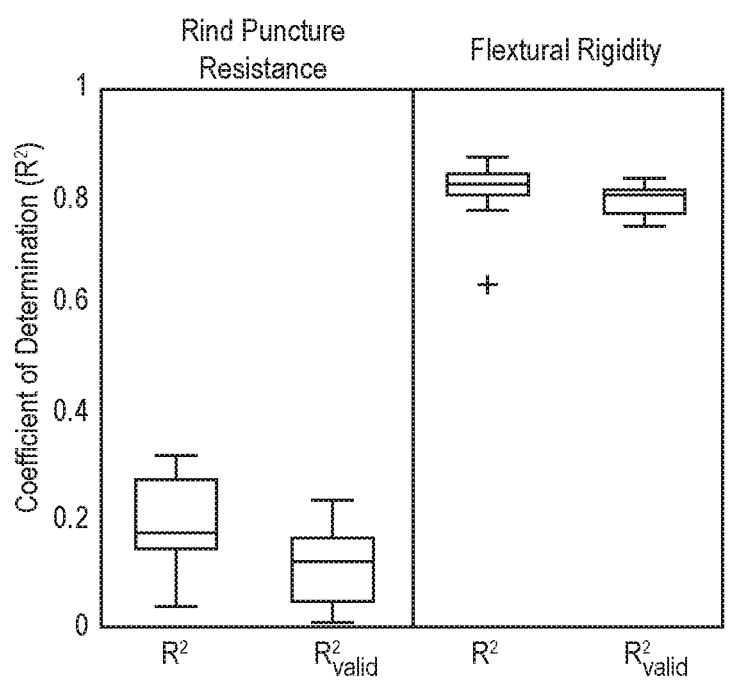
FIG. 10: Box plot distributions of coefficient of determination values for flexural rigidity and rind puncture resistance.

FIG. 10, displays box plots of all of the $R_2$ and $R_{2valid}$ values for FR and RPR which illustrate the systematic differences between RPR and FR as predictors of stalk strength. As expected $R_{2valid}$ values for both FR and RPR tend to be lower than $R_2$ values. However, all $R_{2valid}$ values for FR are above 0.74, indicating a strong pattern of inter-group predictive power. In addition, the variance in $R_2$ and $R_{2valid}$ values is smaller for FR than for RPR.

Discussion

An ideal breeding tool for combating stalk lodging should 1) accurately predict stalk strength, 2) not be confounded by environmental factors or covariates such as hybrid, 3) require minimal effort and time to use and 4) not permanently damage the stalk, thus allowing analysis of individual plants throughout their lifecycle (i.e. collection of temporal data). The consensus among previous researchers is that RPR best adheres to these ideals, and is therefore a good benchmark against which to compare future breeding tools. In the current study, FR outperformed RPR with regards to the aforementioned ideals. In particular, FR was shown to 1) be a better predictor of stalk strength than RPR, 2) FR was not affected by hybrid type, planting density, location, or replicate, whereas RPR was moderately to strongly confounded by such factors and 3) FR does not induce any permanent damage to the stalk whereas RPR requires piercing the stalk rind and pith, thus weakening the structural integrity of the plant and leaving it susceptible to disease. Note that in the current study FR measurements and RPR measurements were acquired after the stalk had been cut and removed from the field. However, it is not necessary to remove stalks from the field to obtain these measurements. FR can be measured by simply deflecting stalks by a few cm and measuring their force and deflection response while standing in the field. Time to phenotype or implement a RPR tool in the field vs time to implement a tool for measuring FR in the field was not evaluated in this study. This remains the subject of the future research. However, as mentioned previously FR can be measured by simply deflecting stalks by a few cm and recording force and displacement data (i.e. stalks do not necessarily have to be loaded in three-point bending), the author's therefore expect FR and RPR to be similar with regards to difficulty of use and time to phenotype.

The bending strength of any structure (including corn stalk) is determined by two governing factors, namely the structures material properties and the structures geometry. For most structures geometry typically dominates the bending response. For example, a recent engineering analysis of corn stalk structure and strength demonstrated that changes in stalk geometry are on average 18 times more influential on stalk mechanical stresses than are changes in material properties. Therefore, selective breeding tools which account for both geometric and material contributions to stalk bending strength will likely outperform tools which focus solely on material properties or stalk chemistry. FR accounts for both geometric and material contributions to stalk strength, whereas RPR primarily measures the material properties of the rind. Furthermore, RPR only measures material properties of the stalk at a single point (the point of needle insertion) whereas the composite FR measure described in this study measures the response of the entire stalk below the ear, including both geometric and material effects. These insights explain why FR is a better predictor of strength than RPR. They also explain why RPR is strongly to moderately affected by the covariates investigated in this study. RPR does not account for geometric contributions to stalk strength, therefore covariates which affect stalk geometry will negatively impact RPR predictions. FR on the other hand does account for geometric contributions to stalk strength and therefore is not negatively affected by covariates which affect stalk geometry. In support of this explanation is the fact that RPR regression line coefficients varied the most and RPR $R_{2valid}$ values were the least when analyzing different planting densities (the covariate which most strongly influences geometry).

Many prevalent problems in crop science are governed by mechanical principals that require engineering expertise to correctly address. Top scientific academies, academic organizations, and policy makers unanimously agree that including engineers in pant research will accelerate research progress and lead to development of breakthrough technologies. This study and others have incorporated the advice of senior leadership with great success and have produced promising results for addressing the long standing problem of stalk lodging. For example in the past two years engineering collaborations have revealed remarkably consistent yet previously unrecognized failure patterns in naturally lodged corn stalk, have illuminated the dominating effects of geometry on stalk strength, have discovered several structural weakness in corn stalk architecture have improved testing methodologies for measuring stalk strength and have identified a potentially transformative breeding tool for developing lodging resistant crop varieties (i.e. flexural rigidity). These advances could not have been achieved by either plant scientist or engineers working in isolation. Similar collaborations will likely lead to rapid advances on numerous fronts in the future.

Limitations—

All hybrids investigated in the current study were commercially available and demonstrate acceptable lodging resistance. Thus, they represent a fairly narrow range possible stalk strength values. Previous studies investigating RPR have generally used commercial and non-commercial maize varieties which represent an extremely broad range of stalk strength values. The use of broad sampling designs employed in previous studies tends to artificially inflate $R_2$ values. For example, some studies have reported correlation values of up to 0.98 for RPR and stalk strength. The current study included only lodging resistant varieties to determine the utility of RPR and FR as breeding tools in late stage breeding trials.

All stalks investigated in the current study were mature and stalk moisture had been reduced to stable levels. This study design was chosen as lodging predominately occurs after stalks have matured and are left to dry in the field. However, results from this study may not be applicable to green stalks. Turgor pressure could change regression line coefficients for both FR and RPR. The ability of FR to determine the strength of green stalks remains the subject of future research.

Conclusion

The purpose of this study was to investigate the utility of FR as a predictor of stalk strength. Results demonstrate that FR is a good predictor of stalk strength and that FR may outperform RPR as a selective breeding tool to improve lodging resistance in the future. FR predictions are not negatively affected by different hybrid types, planting densities, or planting locations. The univariate FR regression line presented in this paper will therefore likely be able to predict the strength of future varieties of corn stalk in the absence of stalk strength measurements. RPR on the other hand was negatively affected by covariates such as hybrid, planting density, location and replicate. Therefore, RPR may not accurately predict the strength of future varieties of corn stalk in the absence of stalk strength measurements (i.e. the strength of future varieties would have to be measured at numerous, planting densities and locations to establish correlations between RPR and strength before RPR could be used to predict strength). In summary, FR may be used to predict the performance of future stalk varieties in the absence of stalk strength measurements and therefore demonstrates potential for becoming an effective breeding tool in combating stalk lodging in the future.

When implementing a cantilevered bending test on corn stalks in the field a strong correlation between flexural rigidity and stalk strength was observed. In particular, data collected on 18 pre-commercial varieties of dent corn demonstrated that stalk flexural rigidity predicted 78% of observed variation in stalk strength (see FIG. 20).

Septate Grass Mechanical Study

Figure 11A:
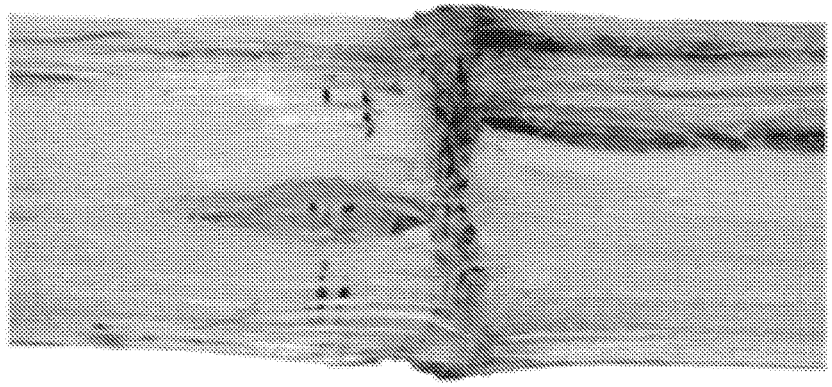
FIGS. 11A-C show longitudinal sections of corn, giant reed, and bamboo. The node of each plant is located at the center of the photograph.
Figure 11B:
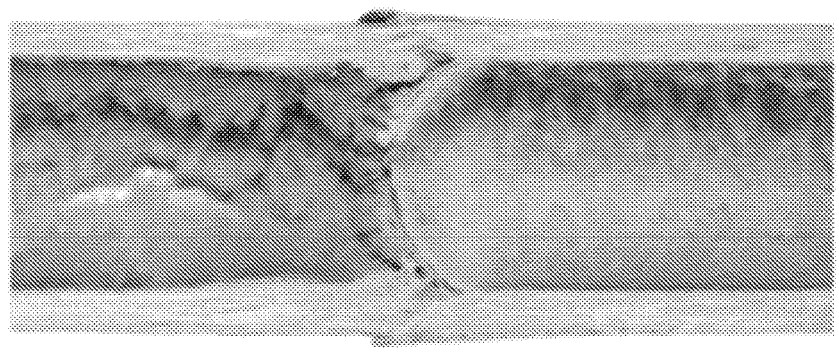
Figure 11C:
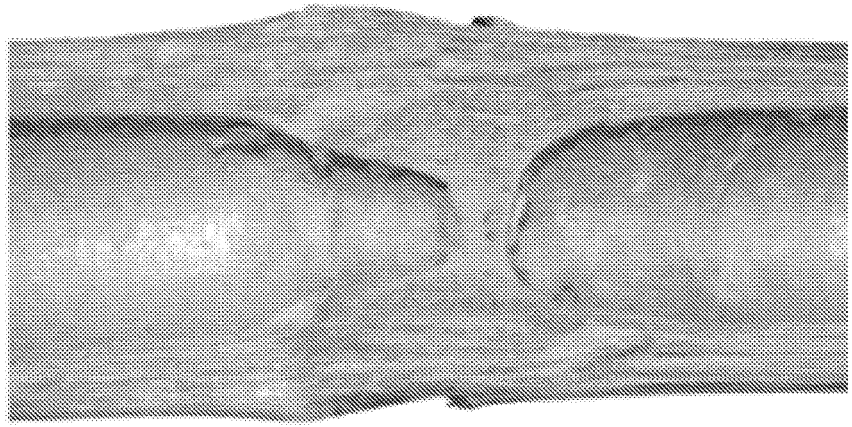

The purpose of this study was to investigate how different loading configurations employed during three-point bending experiments affect test results of septate grass stems and to develop a testing protocol that provides reliable measures of stalk bending strength. On the basis of previous experience testing corn stalks (Robertson et al., 2014), it was hypothesized that loading plant stems at the internode during three-point bending tests induces premature failure by artificially deforming the cross section of the stem, reducing the second moment of area, and thus weakening the overall structure and causing the plant to fail before critical bending stresses have been reached. This hypothesis was tested using three species, bamboo (*Phyllostachys aurea* Carr. ex A. & C. Rivire.), giant reed (*Arundo donax* L.), and maize (*Zea mays* L.). These species were selected for inclusion in the present study because they represent a wide range of geometric and material properties commonly found in septate grass stems. Giant reed is a thin-walled species with very distinct transverse diaphragms at the node. Bamboo is one of the stiffest and strongest grasses, possessing a very large ratio of wall thickness to radius and dense, solid nodes. Unlike the other two species, maize possesses a solid or foam-like parenchyma core, and its nodes are less dense than bamboo but larger and thicker than that of giant reed. FIG. 11 depicts longitudinal sections of each species to highlight these differences.

Materials and Methods

Materials—

The species of bamboo used in the present study was grown commercially and had an average ratio of internodal wall thickness to radius of approximately 0.48. Giant reed was harvested from its natural environment in the United Arab Emirates and had an average wall thickness to radius ratio of 0.18. Maize used in the present study included four precommercial varieties of dent corn grown at Monsanto testing facilities in Iowa and had an average wall thickness to radius ratio of 0.078. The study was limited to mature plants, which were allowed to dry at room temperature and humidity before testing. Plants were dried to allow more direct comparison between species and to eliminate the effect of variables that are difficult to measure or control when testing live tissues (i.e., turgor pressure and numerous biological processes that are affected by the harvesting and sample handling processes). Furthermore, the response of dried bamboo is important to structural building applications, and the response of dried dent corn is relevant to stalk lodging studies. Leaves were removed from each plant, and only those stems exhibiting no visible evidence of disease or pest damage were included in the study.

Mechanical Tests—

Three types of mechanical testing regimes (three-point bending, four-point bending, and transverse compression) were applied to the giant reeds, bamboo culms, and corn stalks investigated. Each of these tests is described in detail below.

Three-Point Bending Tests—

Three-point bending tests were performed in two different loading configurations. In the first configuration, hereafter referred to as "node-loaded", the loading anvil was placed immediately basal to the node line and the supports were placed at adjacent basal and apical nodes. For bamboo and giant reed, supports were located such that two internode regions were being flexed during the test (see FIG. 12A). For maize, four internode regions were flexed during the test. Average span lengths and diameters of test samples±one standard deviation are as follows: span lengths=60±6.1 cm for maize, 35±5.5 cm for giant reed, and 64±11 cm for bamboo; diameters=15.9±1.8 mm for maize, 13.2±0.88 mm for giant reed and 14.2±0.90 mm for bamboo. In the second testing configuration, here after referred to as "internode-loaded", the loading anvil was placed in the center of the adjacent undamaged internode from the node-loaded test and supports were placed 5 cm basal and apical to the loading anvil (10 cm span length). The bending moment was calculated along the entire length of each test specimen during both testing configurations using the standard three-point bending moment equation as follows:

$$M(x) = \begin{cases} \dfrac{Px(L-a)}{L} & 0 \le x \le a \\ \dfrac{Pa}{L}(L-x) & a \le x \le L \end{cases},$$

where P is the applied load, a is the location of the applied load, x is the position along the length of the stalk, L is the span length, and M the moment (see FIG. 12A).

An Instron (Norwood, Mass., USA) 5965 test frame equipped with a 5000-N load cell and a standard loading anvil and supports were used to conduct all tests. The loading anvil was displaced at a rate of 10 cm/min, and load displacement data were recorded every 100 ms just until failure was detected. Failure was defined as the first instance of decrease in load-bearing capacity (i.e., stalk breakage) (Hibbeler and Fan, 2004). Digital photographs were captured during both internode-loaded and node-loaded tests to determine whether significant cross-sectional deformation of the stem was present before failure. To identify differences between test setups, three comparisons were used. First, for each stalk, the bending moment at failure in the node-loaded test was compared with the bending moment at failure in the internode-loaded test. To increase statistical power, adjacent sections of the same stalk were compared. Second, the maximum calculated moment achieved at the center of each internode during the node-loaded test was compared with the maximum moment achieved at the exact same internode during the internode-loaded test. Paired t tests were employed to test for statistical significance in both of these comparisons. The third comparison was made by observing digital photographs that captured the cross-sectional deformation of the stem during each test. Transverse compression tests—Structural transverse stiffness (i.e., resistance to cross-sectional deformation) of bamboo, giant reed, and corn was measured at both nodal and internodal locations. This was accomplished by placing a single supporting anvil directly below the loading anvil (see FIG. 12C). The stem was then placed on the supporting anvil, while the loading anvil was displaced at a rate of 2 mm/min. The test was stopped when the test specimen had deflected by 0.2 mm (reed and corn) or 0.5 mm (bamboo). The small displacement value was used to prevent permanent damage to the test sample. The structural transverse stiffness was determined as the average slope of the resulting force—deformation curve. This process was repeated along the length of stalks at increments of 5 mm (corn and reed) and 10 mm (bamboo).

Four-Point Bending Tests—

Four-point bending tests differ from three-point bending tests in that a large portion of the test sample is subjected to a constant moment (see FIGS. 12B, 2E). Observing the curvature of the test sample in the constant moment region allows one to make conclusions about how the flexural stiffness may change along the length of the sample. In particular, if the curvature of the internodal and nodal regions are similar, then no appreciable difference in flexural stiffness exists between the two regions. If, however, internodes are much stiffer as has been suggested for stem segments of the grass *Arundinaria tecta* (Walt.) Muhl. (Niklas, 1997), then one would observe significant curvature at the nodal region and minimum curvature in the internode regions.

As illustrated in FIG. 12B, each sample in the four-point bending test was supported at the internode regions and loaded at the nodal regions. Loads were applied such that the constant moment region of each sample contained two nodes and three internodes (see FIG. 12B). Optical markers were placed along the length of test samples using permanent ink. A digital camera was oriented perpendicular to the four-point bending test setup such that all optical markers were within the same photographic plane. Calibrated digital photographs of the test sample were captured in both loaded and unloaded states, allowing the total displacement of each optical marker to be calculated.

Results

Three-Point Bending Results—

Figure 13A:
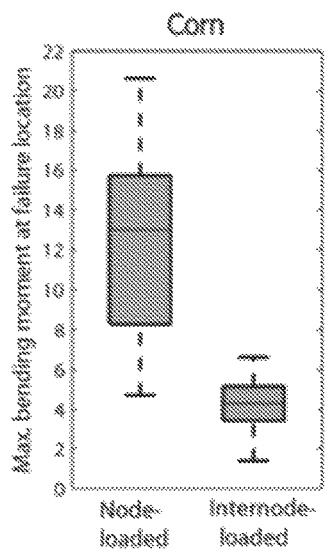
FIGS. 13A-C shows box plots depicting the failure moments of node-loaded and internode-loaded three-point bending experiments of FIG. 13(A) corn, FIG. 13(B) giant reed, and FIG. 13(C) bamboo. For each species, the failure moment is significantly lower (paired t test, P<0.001) in the internode-loaded case, suggesting that the test fixture may be affecting test results (i.e., causing premature failure).
Figure 13B:
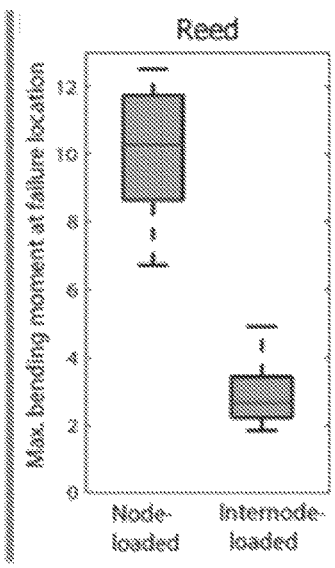
Figure 13C:
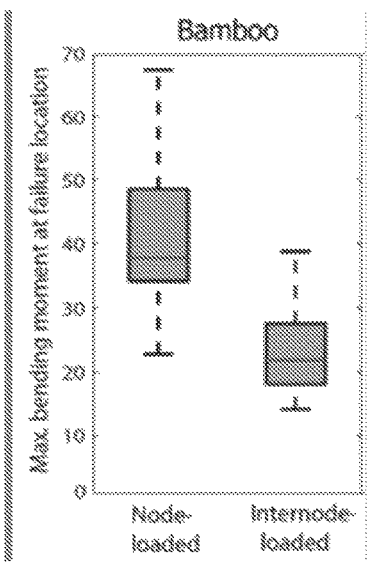

FIG. 13 shows box plots of the maximum moment achieved during the node-loaded and internode-loaded three-point bending tests of corn (n=40), giant reed (n=15), and bamboo (n=14). Results show that all three species failed at much lower moments when loaded at the internode as compared with node-loaded tests (1-tailed paired t test: corn, t=14.2, df=39, P<0.001; giant reed, t=18.1, df=14, P<0.001; bamboo, t=10.5, df=13, P<0.001). On average, the percentage reduction in failure moment between nodeloaded and internode-loaded tests was 64.6% for corn, 70.7% for giant reed, and 44.2% for bamboo. In general, results from internode-loaded tests were not a strong predictor of results from node-loaded tests. The average $R_2$ value of the linear regression line fit to the node-loaded or internode-loaded failure moment data of each species was 0.39.

Figure 14A:
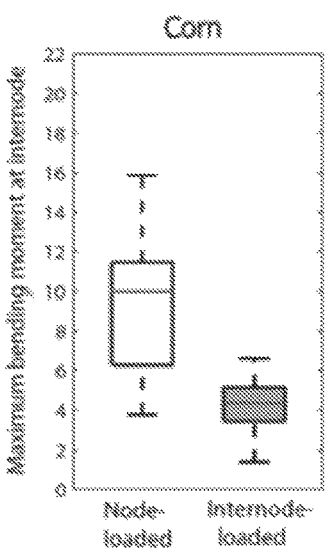
FIG. 14 A-C shows box plots depicting the maximum moment experienced at the center of the internode during both node-loaded and internode-loaded three-point bending experiments of FIG. 14(A) corn, FIG. 14 (B) giant reed, and FIG. 14 (C) bamboo. Unshaded boxes represent data associated with unfailed stalks; shaded boxes represent data associated with failed stalks. For FIG. 14 (A) corn and FIG. 14 (B) giant reed, a significantly larger bending moment was experienced at the internode during the nodeloaded test than was required for the same section to fail during the internode-loaded test (paired t test, P<0.001). For FIG. 14 (C) bamboo, higher moments were observed during internode-loaded tests (paired t test, P<0.01). These results demonstrate that placing the loading anvil at internodal locations during three-point bending experiments induces premature failure in both giant reed and corn stalk. Results for bamboo are inconclusive.
Figure 14B:
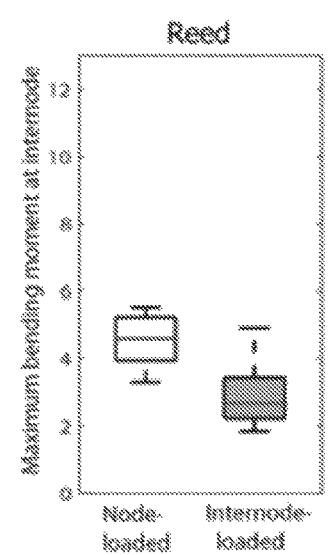
Figure 14C:
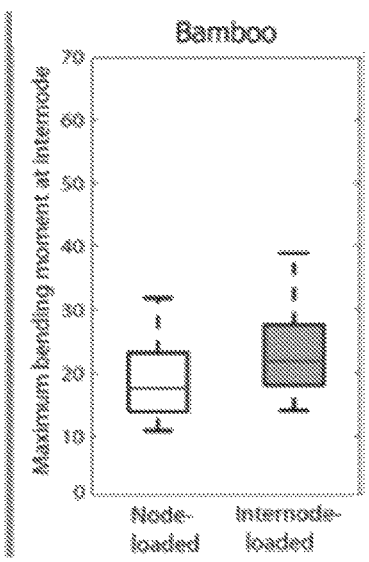
Figure 15A:
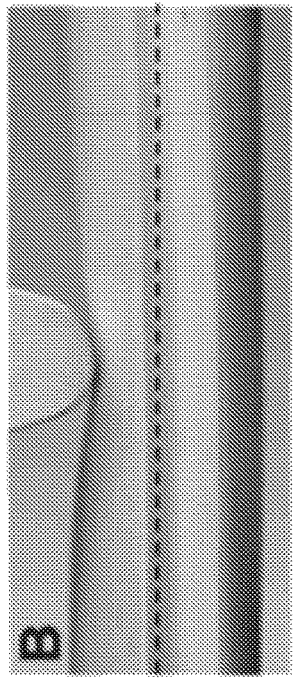
FIGS. 15 A-E illustrate samples tested.
FIGS. 15(B), 15(D), and 15(F) are internode-loaded samples of corn (FIGS. 15(A) and 15(B), giant reed (FIGS. 15(C) and 15(D)), and bamboo (FIGS. 15 (E) and 15 (F)) just before failure. Significant cross-sectional deformation is observed in the internode-loaded cases, and minimal bending deformation is observed FIGS. 15(B), 15(D), and 15(F). The opposite phenomenon is observed in node-loaded tests (significant bending deformation and minimal cross-sectional deformation). These results demonstrate that loading at the internode during three-point bending experiments induces premature failure by significantly reducing the sample's second moment of area (e.g., bending resistivity).
Figure 15B:
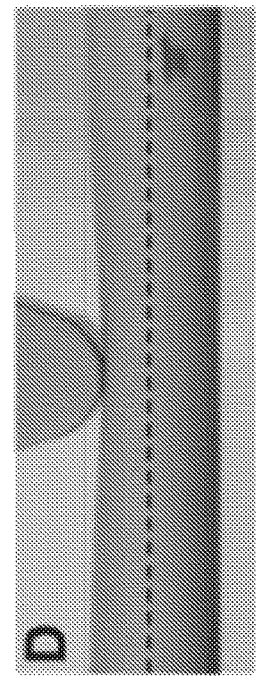
Figure 15C:
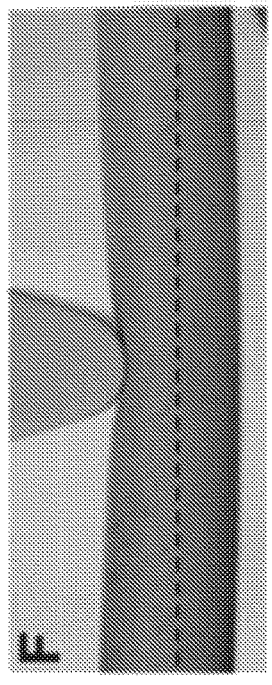
Figure 15D:
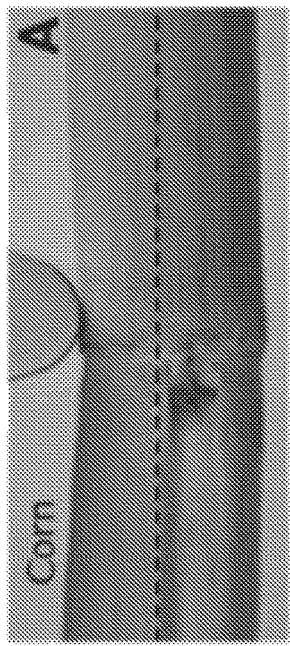
Figure 15E:
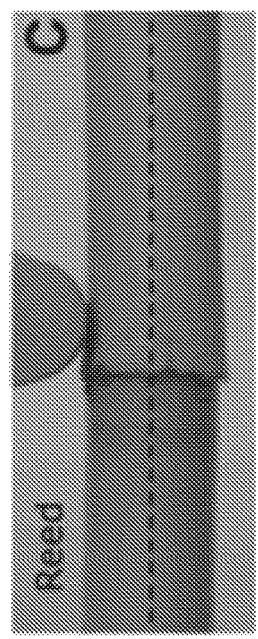
Figure 15F:
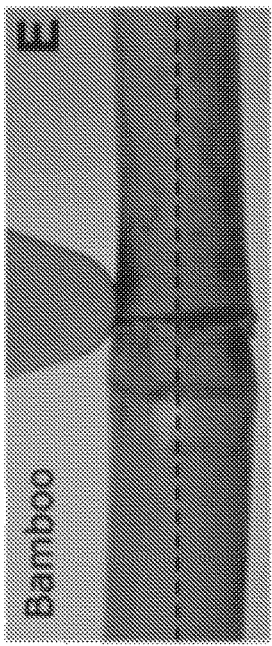

FIG. 14 depicts box plots of the maximum bending moment applied to the center of the same internode during the two loading configurations of interest (internode-loaded and nodeloaded). The unshaded boxes in FIG. 14 indicate that these data are associated with unfailed stalks. In every case, both corn (FIG. 14A) and giant reed (FIG. 14B) were subjected to and supported a higher bending moment at the internode during the node-loaded test than was required to fail the exact same internode during the internode-loaded test (2-tailed paired t test: corn, t=14.1, df=39, P<0.001; giant reed, t=5.6, df=14, P<0.001). These results validated the findings presented in FIGS. 13A and 13B and confirmed that for corn and giant reed, internodal-loadings cause premature stalk failure. For bamboo (FIG. 14C), the failure moment induced at the internode during each internode-loaded test was greater than the moment induced on the same internode during the node-loaded test (2-tailed paired t test: t=3.6, df=13, P<0.01), demonstrating that the node-loading configuration used for bamboo caused the node to fail before the internode failed. However, this result cannot be used to make any conclusions regarding premature failure occurring during internodal testing of bamboo.

During internode-loaded tests (all species), cross-sectional deformation was observed to ensue immediately upon contact of the loading anvil with the test sample. FIG. 15 displays photographs of node-loaded (panels A, C, and E) and internode-loaded (panels B, D, and F) samples of corn, bamboo, and giant reed taken just before failure. These pictures clearly demonstrated that significant transverse deformation of the cross section occurs during internode-loaded testing (panels B, D, and F). In fact, cross-sectional deformation appeared to be the dominating factor in this test (i.e., very little bending deformation was observed). In contrast, the node-loaded samples displayed significant bending deformation and minimal cross-sectional deformation (panels A, C and E of FIG. 15).

Transverse Compression and Cross-Sectional Deformation Results—

Figure 16:
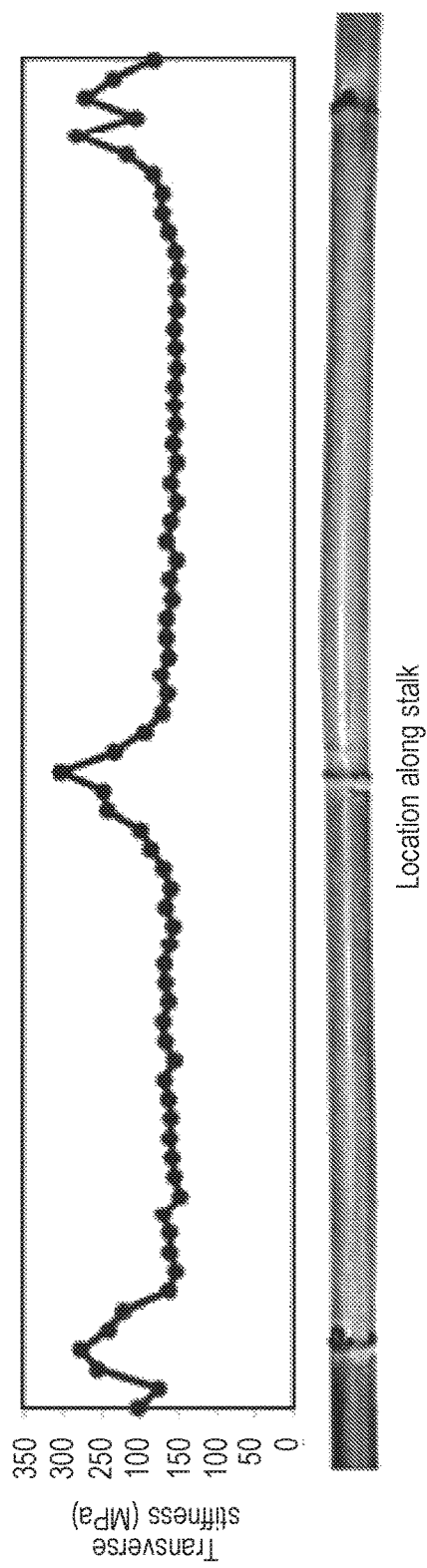
FIG. 16 shows structural transverse compressive stiffness of a typical giant reed measured at 5-mm increments. A photograph of the same reed is shown at the bottom of the figure for reference. Sharp increases in structural transverse compressive stiffness are seen to coincide with nodal regions. Bamboo and corn (not pictured) showed nearly identical trends in transverse stiffness.

Results demonstrated that nodes were substantially more resistant to cross-section deformation than were internode regions (2-tailed t test: corn, t=9.45, df=28, P<0.001; giant reed, t=3.9, df=26, P<0.001; bamboo, t=8.1, df=42, P<0.001). The structural transverse compressive stiffness of a typical giant reed sample is shown in FIG. 16. Very distinct increases in stiffness are seen to coincide with nodal regions. The same trend was observed in both corn and bamboo. For bamboo, the internode was approximately 75% as stiff as the nodal region, while for the giant reed the nodal region was almost twice as stiff as the internode. Results for corn stalk showed that the transverse structural stiffness of the nodes was more than twice that of the internodes. This trend in structural transverse compressive stiffness is a direct consequence of the geometric structure of septate grass stems (i.e., wall thickness increases substantially near nodes, and in some cases, the nodes are completely solid).

Four-Point Bending Results—

Figures 17A, 17B, 17C:
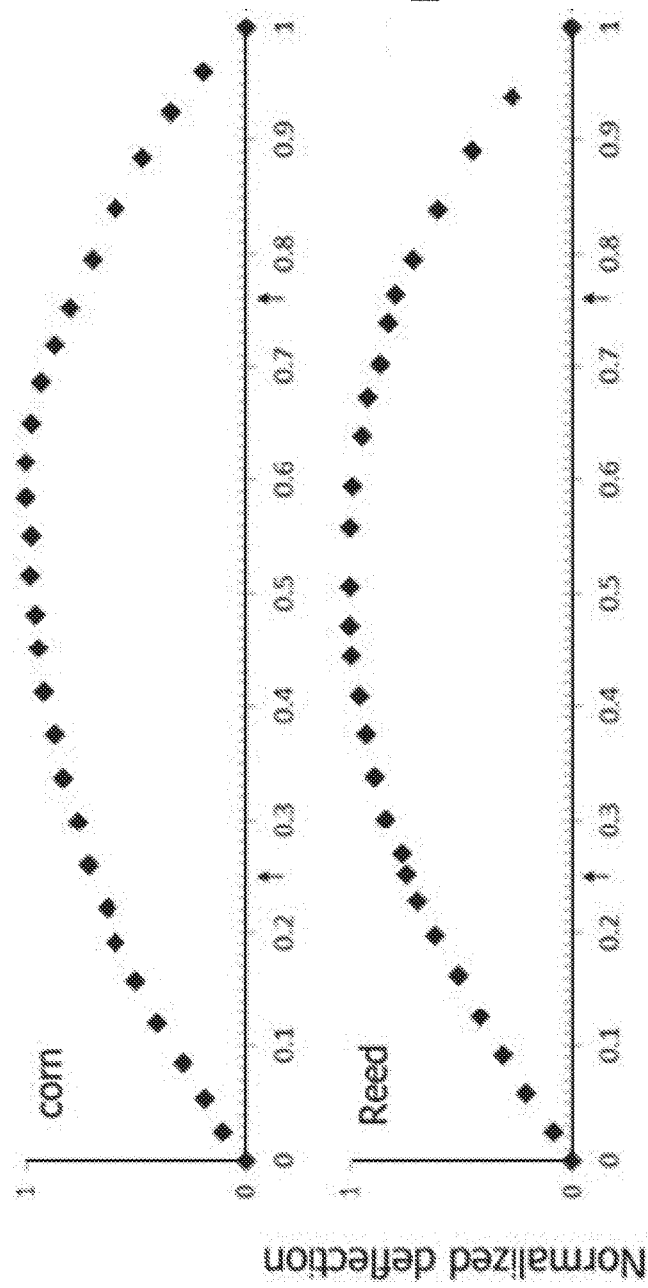
FIGS. 17A-C show vertical displacement of optical markers located in the constant moment region of four-point bending tests of FIG. 17(A) corn, FIG. 17 (B) giant reed, and FIG. 17 (C) bamboo. Significant flexural deformation is seen to occur along the entire length of each stalk. Locations of nodes are indicated by arrows placed along the horizontal axis.

Four-point bending tests were performed on nine samples (three for each species). FIG. 17 displays the typical displacement patterns of the stalks relative to an imaginary straight line drawn between the two loading points, (i.e., the constant moment region). All species displayed significant flexural deformation (i.e., curvature>0) at both nodal (1-sample 2-tailed t test: corn, t=3.6, df=33, P<0.001; 0.001) and internodal locations (1-sample 2-tailed t test: corn, t=5.5, df=109, P<0.001; reed, t=7.0, df=41, P<0.001; bamboo, t=13.0, df=134, P<0.001). For bamboo (FIG. 17C) and giant reed (FIG. 17B), the change in curvature along the stalk was remarkably smooth, indicating that the overall bending stiffness did not differ between the node and internode.

Discussion

Loading Configuration of Three-Point Bending Test—

Results presented in FIGS. 14A and 14B confirmed the first hypothesis of this study, that loading thin-walled plant stems (i.e., maize and giant reed) at the internode during three-point bending tests would result in inaccurate bending strength measurements (i.e., stems break long before critical bending stresses are reached). Considering the levels of transverse deformation apparent in FIG. 15C and the reduction in failure moment displayed in FIG. 13C, it seems plausible that internode loadings can also cause premature failure in thick-walled plant stems like bamboo. However, it is important to realize that some of the difference between the node-loaded and internode-loaded failure moments presented in FIG. 13C could be due to structural and material difference between the two regions and not only due to the test instrument inducing premature failure in internode-loaded tests. Similar results have not been reported previously and are especially relevant to plant biomechanics and agronomic breeding studies focused on measuring plant phenotypes or on improving bending strength of septate plant stems.

When hollow tubular structures (e.g., plant stems) are subjected to bending moments, their cross sections ovalize, and once a critical bending force is reached, the outermost layer of the tube will permanently crimp (Spatz et al., 1990; Niklas, 1992, 1997; Spatz and Niklas, 2013). This crimping is a local phenomenon referred to as brazier buckling. It has been hypothesized that, in septate plant stems, one function of the nodes is to act as a stiffener, reducing the amount of cross-sectional ovalization, thus delaying the onset of brazier buckling (Niklas, 1989, 1997; Spatz et al., 1990, 1997; Schulgasser and Witztum, 1992, 1997). Results from the present study support this hypothesis. Under transverse compression, nodes were significantly stiffer and able to support much higher loads than internodes (FIG. 16) and therefore serve as mechanical braces. When concentrated transverse loads (e.g., loading anvil) were applied away from these mechanical braces during internode-loaded bending experiments, obvious cross-sectional deformation occurred before failure (see panels B, D, and F of FIG. 15). Such deformation reduces the bending strength, leading to artificially induced buckling.

To obtain accurate data regarding stem failure, three-point bending tests should be designed so that failure occurs away from load and attachment points. General engineering principles predict that artificially high stresses develop at these locations, which can initiate premature stem failure. For example, when conducting three-point bending test on typical engineering materials (metals, plastics, ceramics, and even wood), failure typically happens on the tensile side of the beam (away from the loading anvil). However, in internode-loaded tests of plant stems, failure always occurred directly beneath the loading anvil (compressive side of the beam or stem), which created a single straight crease across the stalk. In other words, failure location of internode-loaded tests is not determined by a material or structural weakness, but by the testing instrument itself. In addition, the majority of deformation that occurs in internode-loaded test appears to be cross-sectional deformation; thus, the samples likely failed as a result of transverse compressional stresses combined with shear and bending stresses.

Nodal-loading of plant stems did not suffer from the various shortcomings and errors produced by internodal loadings. First, little to no cross-sectional deformation was observed during nodal loadings. Second, failure happened away from loading and attachment points where artificially high stresses occur. Third, the failure patterns produced were typical of plant stems that have failed in their natural environment. In particular, 94% of the tests resulted in failure occurring just above the loaded node in or near the meristematic tissue region (away from loading and attachment points), with crease patterns or splitting in the stalk that could not be predicted before the test (as is typical of biological systems). These results are consistent with reported failure patterns of septate plant stems that failed in their natural loading environments (Niklas, 1989, 1992; Robertson et al., 2014). A summary of comparisons between node-loaded and internode-loaded results is provided in Table 3.

The Influence of Span Length—

In three-point bending experiments, the applied moment is a function of both span length and applied load. As the span length in the three-point bending experiments increases, the force required to achieve a prescribed moment decreases (Eq. 1). Therefore, by increasing span length, the force imposed by the loading anvil and subsequent cross-sectional deformation can be minimized. When short span lengths are used, however, the amount of cross-sectional deformation and shear stress is increased. Even when loading at the node, premature failure may be induced if short span lengths are employed. Theoretically, one could load plant stems at the internode without producing premature failure if the span length was sufficiently large. However, even internode-loaded tests conducted in the laboratory utilizing long span lengths (250 cm) have always produced a single creasetype failure directly below the loading anvil and significant cross-sectional deformation before failure.

Node and Internode Bending Stiffness—

Results from the four-point bending tests suggest that in general, nodes do not act as "flexible joints" as is sometimes suspected (FIG. 17) (Niklas, 1997). Significant geometric and material differences occur at nodes (both of which affect flexural stiffness). When observing bending experiments with the naked eye, stalks do appear to flex more near nodal regions; however, plots of displacement (FIG. 17) and subsequent analysis suggest that this is not the case. It is believe that the visual impression that bending occurs primarily at the nodes is an optical illusion caused by a stalk architecture which appears to consist of straight individual segments. Curvature of the stalk profile between nodes may contribute to this optical effect. This optical effect can easily be removed by tracking markers during bending experiments. A dedicated study on this topic may be required to definitively address this issue.

Structural bending stiffness is governed by two factors: tissue stiffness and sample geometry (i.e., moment of inertia). Results from four-point bending tests of bamboo and giant reed suggest that geometric changes near the node (increased diameter and rind thickness) compensate for any reductions in tissue stiffness that occur in the same region such that the overall flexural stiffness of the plant remains nearly constant in and around the node. Mechanical or biological reasons that plants display this trait are unclear.

loaded three-point bending tests induce failure that is (1) premature, (2) occurs in the wrong location, (3) is unrelated to natural failure modes and patterns, and (4) these tests induce high levels of transverse compression and shear such that the measured response of the sample is not actually a flexural response, but a combination of flexure, compression, and shear. As such, any material property data, failure mode analysis, or investigations that depend on these measures (e.g., stalk lodging, turgor effects, oscillation frequencies of stems) will suffer adverse effects if internode-loaded three-point bending is used. The overall trends presented in previous studies that have used this test setup will likely not change in the future (e.g., turgor definitely increases bending stiffness), but the degree of change and absolute value of flexural properties measured in such studies has been negatively affected. It is possible that in some cases, studies using internodal three-point bending experiments could have produced a different conclusion if a sound testing methodology (e.g., nodal loadings) had been used.

TABLE 3

| Character | Node-loaded | Internode-loaded |
| --- | --- | --- |
| Failure location | Varied: near, but not at load point | Uniform: all failure occurs at load point |
| Failure appearance | Unique: each failure pattern is different | Uniform: a straight crease formed in all samples |
| Cross-sectional deformation | No apparent deformation | Obvious cross-sectional deformation |
| Cross-sectional stiffness at load point | High: significantly more physiological structure at node | Low: hallow or pith-filled structure with thin rind |
| Bending stiffness | Accurate: almost all deformation is due to bending | Inaccurate: significant transverse deformation in addition to bending |
| Moment at failure | Accurate: failure not affected by the leading apparatus | Inaccurate: premature failure induced by test configuration |

Limitations—

The primary limitation of this study was the use of dried (nonliving) tissues. The decision to use this approach was based upon the authors' experience in biomedical engineering studies in which tissue handling and preparation contributes to large amounts of sample variability and can complicate attempts at replication and comparison. By using dried tissue, the effects of variables that are difficult to measure and control (turgor, biological processes) are eliminated, thus allowing a more direct comparison between species. A natural limitation of this approach is that the measurements reflect only the nonliving structure of the plants studied (e.g., cellulose, hemicellulose, lignin).

While moisture and turgor are expected to modify the stiffness and strength of plant stems, such variables are unlikely to influence the primary findings of this study, which are strongly based on geometric factors. The following findings of this study can be extended to provide insights on living tissues. First, creases that form at the loading anvil indicate that the test setup is inducing premature failure of the sample. Second, artificial cross-sectional deformation of the sample can be reduced by maximizing span length and using a blunt or rounded loading anvil. Third, nodes are more dense and solid than internodes and mechanically act as transverse bracing. Therefore, placing the loading anvil at nodal locations serves to minimize transverse deformation of the sample and can greatly increase the accuracy of three-point bending experiments. These findings are relevant for future studies, regardless of whether the samples are living or dried.

Relevance to Other Research—

Accurate and reliable testing methodologies are a fundamental tenet of scientific research, and three-point bending of isolated internodal segments has been shown to be an unsound practice. As such, it should be strongly discouraged in the future. Results herein demonstrate that internode- Conclusion Four types of mechanical tests were performed on bamboo (*Phyllostachys aurea* Carr. ex A. & C. Rivire.), giant reed (*Arundo donax* L.), and maize (*Zea mays* L.) to test the hypothesis that internodal loading of septate plant stems results in inaccurate bending strength measurements. This hypothesis is confirmed by observations summarized in Table 1. Nodeloaded tests did not suffer from the various inaccuracies of internode-loaded three-point bending experiments. The following principles or guidelines described above with regard to the apparatus were determined from the results of this study to aid accurately measure the bending strength of septate grass stems via three-point bending experiments:

(1) The loading anvil should be placed immediately basal to the node line (panels A, C and E of FIG. 15) and not in the middle of an internode section.

(2) The span length should be maximized to reduce the transverse load required to achieve a bending moment on the sample. In general, span lengths shorter than 20×the diameter of the sample should not be employed.

(3) The shape of the loading anvil and supports should have no sharp corners or edges but rather be rounded (as seen in FIG. 15) to maximize contact between the sample and loading instrument, thus distributing transverse forces over a larger area of the sample.

(4) Crosshead speeds (i.e., rate of deflection) should be chosen to minimize viscoelastic effects. At very slow speeds, stress relaxation will occur, and at very fast speeds, strain hardening will occur. Crosshead speeds used in the present study are a good starting point, but ultimately the required speed will depend on numerous factors, including test setup, species, moisture content of the sample, etc.

(5) Both nodal and internodal tissues should be flexed during any test that intends to produce results generalizable to the entire stem or stalk (Niklas, 1997).

Further its believe the following should be considered as a best practice as well: (1) failure should occur away from sample support and loading points, (2) the test setup should not artificially induce cross-sectional deformation of the sample, and (3) the types and location of failure should be similar to those found in the natural loading environment.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A testing apparatus comprising:
    a base;
    a support pivotable about a hinge with respect to the base, the support is directly coupled to the base by the hinge;
    a contact element adjustably engaged with the support;
    a force gauge associated with the contact element; and
    a displacement sensor associated with the hinge and configured to detect angular displacement of the support.

2. The testing apparatus of claim 1, wherein the base has a substantially flat lower surface and a plurality of spikes extending downward therefrom.

3. The testing apparatus of claim 1, wherein the base has a notch therethrough.

4. The testing apparatus of claim 1, wherein the support comprises a first hinged arm and a second hinged arm parallel to each other.

5. The testing apparatus of claim 4, wherein the contact element is slidable along the first hinged bar and the second hinged bar.

6. The testing apparatus of claim 1, further comprising a computer processor and memory in communication with the force gauge and the displacement sensor.

7. A method of determining the flexural rigidity of a plant comprising:
    setting a base adjacent the plant base;
    adjusting a contact element along a support and aligning the contact element with a stem of the plant;
    angularly displacing the support and engaging the stem with the contact element to apply force to the stem;
    further comprising determining a height of the contact element from ground;
    measuring force data concerning the force applied to the stem;
    measuring angular displacement of the support associated with the measured force data; and
    determining from the force data and angular displacement the flexural stiffness of the stem.

8. The method of claim 7, wherein the base is secured to a surface.

9. The method of claim 7, wherein the plant is positioned within a groove in the base.

10. The method of claim 7, wherein aligning the contact element with the stem of the plant comprises positioning the contact element perpendicular with the stem.

11. The method of claim 7, wherein the flexural rigidity is correlated with a strength of the plant stem.

12. A method of determining plant stem strength comprising:
    engaging the plant stem with a testing apparatus;
    detecting force applied to the stem;
    displacing the plant stem;
    measuring angular displacement of the stem associated with the force; and
    determining at least one of flexural rigidity and bending strength of the plant stem.

13. The method of claim 12, wherein the testing apparatus is a wearable device.

14. The method of claim 12, wherein the testing apparatus is a handheld device.

15. The method of claim 12, wherein detecting the force applied comprises receiving pressure information from one or more pressure sensors.

16. The method of claim 12, wherein engaging the plant stem comprises pivoting a contacting element of the testing apparatus.

17. The method of claim 12, wherein engaging the plant stem comprises engaging a nodal region of the stem.

18. The method of claim 12, further comprising determining a height of the testing apparatus from ground.

* * * * *

UNITED STATES PATENT AND TRADEMARK OFFICE
CERTIFICATE OF CORRECTION

| | | |
|---|---|---|
| PATENT NO. | : 10,337,951 B2 | Page 1 of 1 |
| APPLICATION NO. | : 15/736274 | |
| DATED | : July 2, 2019 | |
| INVENTOR(S) | : Douglas Cook et al. | |

It is certified that error appears in the above-identified patent and that said Letters Patent is hereby corrected as shown below:

In the Specification

Column 1, following after the "Cross Reference to Related Applications" sub-heading and paragraph, add new sub-heading and paragraph:
STATEMENT OF GOVERNMENT INTEREST
"This invention was made with government support under grant number CMMI1400973 awarded by the National Science Foundation. The government has certain rights in the invention."

Signed and Sealed this
First Day of April, 2025

Coke Morgan Stewart
*Acting Director of the United States Patent and Trademark Office*